US009024033B2

(12) United States Patent
Witty et al.

(10) Patent No.: US 9,024,033 B2
(45) Date of Patent: May 5, 2015

(54) ANTI-MALARIAL AGENTS

(75) Inventors: Michael John Witty, Dover (GB); David Hardick, Stretham (GB)

(73) Assignee: MMV Medicines for Malaria Venture, Geneva (CH)

( * ) Notice: Subject to any disclaimer, the term of this patent is extended or adjusted under 35 U.S.C. 154(b) by 0 days.

(21) Appl. No.: 13/522,775

(22) PCT Filed: Jan. 17, 2011

(86) PCT No.: PCT/IB2011/050192
§ 371 (c)(1),
(2), (4) Date: Jul. 18, 2012

(87) PCT Pub. No.: WO2011/086531
PCT Pub. Date: Jul. 21, 2011

(65) Prior Publication Data
US 2012/0295905 A1    Nov. 22, 2012

Related U.S. Application Data

(60) Provisional application No. 61/295,821, filed on Jan. 18, 2010.

(51) Int. Cl.
| | |
|---|---|
| *C07D 213/73* | (2006.01) |
| *C07D 401/04* | (2006.01) |
| *C07D 401/10* | (2006.01) |
| *C07D 401/14* | (2006.01) |
| *C07D 413/04* | (2006.01) |
| *C07D 413/10* | (2006.01) |
| *C07D 413/14* | (2006.01) |
| *C07D 417/10* | (2006.01) |
| *C07D 417/14* | (2006.01) |
| *C07D 213/74* | (2006.01) |
| *C07D 405/04* | (2006.01) |
| *C07D 417/04* | (2006.01) |
| *C07D 471/04* | (2006.01) |

(52) U.S. Cl.
CPC ............ *C07D 213/73* (2013.01); *C07D 213/74* (2013.01); *C07D 401/04* (2013.01); *C07D 401/10* (2013.01); *C07D 401/14* (2013.01); *C07D 405/04* (2013.01); *C07D 413/04* (2013.01); *C07D 413/10* (2013.01); *C07D 413/14* (2013.01); *C07D 417/04* (2013.01); *C07D 417/14* (2013.01); *C07D 471/04* (2013.01)

(58) Field of Classification Search
CPC .. C07D 401/04; C07D 401/10; C07D 401/14; C07D 413/04; C07D 413/10; C07D 413/14; C07D 417/10; C07D 417/14
See application file for complete search history.

(56) References Cited

U.S. PATENT DOCUMENTS 7,220,863 B2    5/2007    Park et al.

FOREIGN PATENT DOCUMENTS

| CN | 101555248 | 10/2009 |
|---|---|---|
| WO | WO 2007/032016 | 3/2007 |
| WO | WO 2008/025820 | 3/2008 |
| WO | WO 2008025820 A1 * | 3/2008 |

OTHER PUBLICATIONS

Hilton, S. et al. "Identification and characterisation of 2-aminopyridine inhibitors of checkpoint kinase 2" *Bioorganic & Medicinal Chemistry*, 2010, pp. 707-718, vol. 18.
Gamo, F.-J. et al. "Thousands of chemical starting points for antimalarial lead identification" *Nature*, May 20, 2010, pp. 305-310, vol. 465.
Zang, Y. et al. "5-Substituted Derivatives of 6-Halogeno-3-((2-(S) azetidinyl)methoxy)pyridine and 6-Halogeno-3-((2-(S)-pyrrolidinyl)methoxy)pyridine with Low Picomolar Affinity for α4β2 Nicotinic Acetylcholine Receptor and Wide Range of Lipophilicity: Potential Probes for Imaging with Positron Emission Tomography" *Journal of Medicinal Chemistry*, 2004, pp. 2453-2465, vol. 47.
Miyaura, N. et al. "Palladium-Catalyzed Cross-Coupling Reactions of Organoboron Compounds" *Chemical Reviews*, 1995, pp. 2457-2483, vol. 95.
Thompson, A. E. et al. "Palladium-Catalyzed Cross-Coupling Reactions of Pyridylboronic Acids with Heteroaryl Halides Bearing a Primary Amine Group: Synthesis of Highly Substituted Bipyridines and Pyrazinopyridines" *Journal of Organic Chemistry*, 2005, pp. 388-390, vol. 70.
Younis, Y. et al. "3,5-Diaryl-2-aminopyridines as a Novel Class of Orally Active Antimalarials Demonstrating Single Dose Cure in Mice and Clinical Candidate Potential" *Journal of Medicinal Chemistry*, 2012, pp. 3479-3487, vol. 55.
Written Opinion in International Application No. PCT/IB2011/050192, Jul. 11, 2011, pp. 1-10.
Paquet, T. et al. "Antimalarial aminothiazoles and aminopyridines from phenotypic whole-cell screening of a SoftFocus® library" *Future Med. Chem.*, 2012, 2265-2277, vol. 4, No. 18.
Younis, Y. et al. "Cell-Based Medicinal Chemistry Optimization of High Throughput Screening Hits for Orally Active Antimalarials. Part 2: Hits from SoftFocus Kinase and other Libraries" *Journal of Medicinal Chemistry*, 2013, pp. 7750-7754, vol. 56.
Bracher, F. et al. "Total Synthesis of the Indolizidinium Alkaloid Ficuseptine" *Eur. J. Org. Chem.*, 2002, pp. 2288-2291.
Gamo, F. et al. "Thousands of chemical starting points for antimalarial lead identification" *Nature*, May 20, 2010, pp. 305-312, vol. 465.

(Continued)

*Primary Examiner* — Timothy Thomas
(74) *Attorney, Agent, or Firm* — Saliwanchik, Lloyd & Eisenschenk

(57) ABSTRACT

The present invention is related to a use of aminopyridine derivatives in the manufacture of a medicament for preventing or treating malaria. Specifically, the present invention is related to aminopyridine derivatives useful for the preparation of a pharmaceutical formulation for the inhibition of malaria parasite proliferation.

10 Claims, No Drawings

(56) References Cited

OTHER PUBLICATIONS

González Cabrera, D. et al. "Structure-Activity Relationship Studies of Orally Active Antimalarial 3,5-Substituted 2-Aminopyridines" *Journal of Medicinal Chemistry*, 2012, pp. 11022-11030, vol. 55.

Database NCBI, PubChem Compound, Compound Summary for: CID 44525557, TCMDC-133347, May 19, 2010, retrieved from the Internet, URL: http://pubchem.ncbi,nlm.nih.gov/, pp. 1-3.

Database NCBI, PubChem Compound, Compound Summary for: CID 44525553, TCMDC-133343, May 19, 2010, retrieved from the internet, URL: http://pubchem.ncbi,nlm.nih.gov/, pp. 1-4.

Database NCBI, PubChem Compound, Compound Summary for: CID 24821157, TCMDC-133348, May 19, 2010, retrieved from the internet, URL: http://pubchem.ncbi,nlm.nih.gov/, pp. 1-3.

Database NCBI, PubChem Compound, Compound Summary for: CID 44525559, TCMDC-133350, May 19, 2010, retrieved from the internet, URL: http://pubchem.ncbi,nlm.nih.gov/, pp. 1-3.

Database NCBI, PubChem Compound, Compound Summary for: CID 44525554, TCMDC-133344, May 19, 2010, retrieved from the internet, URL: http://pubchem.ncbi,nlm.nih.gov/, pp. 1-3.

Database NCBI, PubChem Compound, Compound Summary for: CID 44525560, CHEMBL531475, May 19, 2010, retrieved from the internet, URL: http://pubchem.ncbi,nlm.nih.gov/, pp. 1-5.

* cited by examiner

ANTI-MALARIAL AGENTS

CROSS-REFERENCE TO RELATED APPLICATIONS

This application is the U.S. national stage application of International Patent Application No. PCT/IB2011/050192, filed Jan. 17, 2011, which claims the benefit of U.S. Provisional Patent Application No. 61/295,821, filed Jan. 18, 2010.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum* is the dominant species in sub-Saharan Africa, and is responsible for the almost 1 million deaths each year. The disease burden is heaviest in African children under 5 years of age and in pregnant women. *Plasmodium vivax* causes 25-40% of the global malaria burden, particularly in South and Southeast Asia, and Central and South America. The other two main species that are known to infect humans are *Plasmodium ovale* and *Plasmodium malariae*.

Malaria is a disease that is prevalent in many developing countries. Approximately 40% of the world's population lives in countries where the disease is endemic; approximately 247 million people suffer from the disease every year.

Various medications are presently used for the treatment of malaria. However, many of these medications are costly and some exhibit significant toxicity and undesirable side effects in humans. The most common drug for treating malaria is chloroquine. Other drugs include quinine, mefloquine, atovaquone/proguanil, doxycycline, artesunate, hydroxychloroquine, halofantrine, pyrimethamine-sulfadoxine, and primaquine.

However, the widespread emergence of drug resistance of malaria parasites in many tropical countries has compromised many of the current chemotherapies and there is a continued need for new chemotherapeutic approaches. Accordingly, this invention provides novel potent anti-malarial agents and methodology of treating malaria using novel potent anti-malarial agents.

SUMMARY OF THE INVENTION

The present invention is directed towards aminopyridine derivatives useful in the treatment and/or prophylaxis of malaria, pharmaceutical formulation, use and manufacture thereof.

A first aspect of the invention provides a use of an aminopyridine derivative according to the invention or a pharmaceutically acceptable salt thereof or a pharmaceutically active derivative thereof, for the preparation of a pharmaceutical composition for the prevention and/or treatment of malaria.

A second aspect of the invention relates to an aminopyridine derivative according to the invention or a pharmaceutically acceptable salt thereof or a pharmaceutically active derivative thereof, for the prevention and/or treatment of malaria.

A third aspect of the invention relates to aminopyridine derivatives according to the invention, pharmaceutical formulations thereof and use as a medicament thereof.

A fourth aspect of the invention resides in a method for preventing and/or treating malaria in a patient. The method comprises administering an aminopyridine derivative, or a pharmaceutically acceptable salt or a pharmaceutically active derivative thereof in a patient in need thereof.

A fifth aspect of the invention provides a process for the preparation of an aminopyridine derivative according to the invention and intermediates thereof.

A seventh aspect of the invention provides an intermediate of Formula (iv) according to the invention.

An eighth provides an intermediate of Formula (viii) according to the invention.

A ninth aspect provides an intermediate of Formula (iii) or (v) according to the invention. Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "$C_1$-$C_6$ alkyl" when used alone or in combination with other terms, comprises a straight chain or branched $C_1$-$C_6$ alkyl which refers to monovalent alkyl groups having 1 to 6 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, and the like.

The term "$C_2$-$C_6$ alkenyl" when used alone or in combination with other terms, comprises a straight chain or branched $C_2$-$C_6$ alkenyl. Particularly, it refers to groups having 2 to 6 carbon atoms and having at least 1 or 2 sites of alkenyl unsaturation. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like. Among others, are vinyl or ethenyl (—CH=$CH_2$), n-2-propenyl (allyl, —$CH_2$CH=$CH_2$), isopropenyl, 1-propenyl, 2-methyl-1-propenyl, 1-butenyl, 2-butenyl, and 3-methyl-2-butenyl and the like.

The term "$C_2$-$C_6$ alkynyl" when used alone or in combination with other terms, comprises a straight chain or branched $C_2$-$C_6$ alkynyl. It may have any available number of triple bonds in any available positions. This term is exemplified by groups such as alkynyl groups that may have a carbon number of 2-6, and optionally a double bond, such as ethynyl (—C≡CH), 1-propynyl, 2-propynyl (propargyl: —$CH_2$C≡CH), 2-butyryl, 2-pentene-4-ynyl, and the like.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxyethyl and the like.

The term "aryl" refers to an unsaturated aromatic carbocyclic group of from 6 to 14 carbon atoms having a single ring (e.g. phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, isoquinolinyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyridol[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_2$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g. cyclohexyl) or multiple condensed rings (e.g. norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl) methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to alkyl groups having an acyloxy substituent, including 2-(ethylcarbonyloxy)ethyl and the like.

The term "alkoxy" refers to the group —O—R where R includes optionally substituted "$C_1$-$C_6$ alkyl", optionally substituted "aryl", optionally substituted "heteroaryl", optionally substituted "aryl $C_1$-$C_6$ alkyl" or optionally substituted "heteroaryl $C_1$-$C_6$ alkyl".

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to $C_1$-$C_6$ alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocyclo alkyl," "aryl," "hetero aryl," "aryl $C_1$-$C_6$ alkyl", "heteroaryl $C_1$-$C_6$ alkyl", "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R' and R" are independently H, "$C_1$-$C_6$ alkyl," "$C_2$-$C_6$ alkenyl," "$C_2$-$C_6$ alkynyl," "$C_3$-$C_8$-cycloalkyl," "heterocyclo alkyl," "aryl," "hetero aryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_2$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$-alkyl groups having an ureido substituent, including 2-(N'-methylureido)ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl hetero aryl", "$C_3$-$C_8$-cycloalkyl," or "heterocycloalkyl," and where R and R', together with the nitrogen atom to which they are attached, can optionally form a 3-8-membered heterocycloalkyl ring.

The term "amino $C_1$-$C_6$ alkyl" refers to alkyl groups having an amino substituent, including 2-(1-pyrrolidinyl)ethyl and the like.

The term "ammonium" refers to a positively charged group —$N^+$RR'R" where R, R' and R" are independently "$C_1$-$C_6$ alkyl", "$C_1$-$C_6$ alkyl aryl", "$C_1$-$C_6$ alkyl heteroaryl," "$C_3$-$C_8$-cycloalkyl," or "heterocycloalkyl," and where R and R', together with the nitrogen atom to which they are attached, can optionally form a 3-8-membered heterocycloalkyl ring.

The term "ammonium $C_1$-$C_6$ alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "$C_2$-$C_6$ $C_2$-$C_6$ alkynyl," "$C_3$-$C_8$-cycloalkyl," "heterocycloalkyl," "aryl," "heteroaryl," "aryl $C_1$-$C_6$ alkyl," "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfamate" refers to a group —OSO$_2$—NRR' wherein R and R' are independently selected from H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroarylaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and the like.

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl," "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl)ethyl and the like.

The term "sulfinyl" refers to a group "—S(O)—R" wherein R is selected from "$C_1$-$C_6$ alkyl," "$C_1$-$C_6$ alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "hetero aryl," "aryl $C_1$-$C_6$ alkyl," "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl $C_1$-$C_6$ alkyl" refers to alkyl groups having a sulfinyl substituent, including 2-(methylsulfinyl)ethyl and the like.

The term "sulfanyl" refers to groups —S—R where R includes H, halogens, e.g. a —SF$_5$ group, optionally substituted "$C_1$-$C_6$ alkyl," in particular "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocyclo alkyl," "aryl," "hetero aryl," "aryl $C_1$-$C_6$ alkyl," "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "$C_3$-$C_8$-cycloalkyl $C_1$-$C_6$ alkyl," or "heterocycloalkyl $C_1$-$C_6$ alkyl".

The term "sulfanyl $C_1$-$C_6$ alkyl" refers to $C_1$—O$_5$-alkyl groups having a sulfanyl substituent, including 2-(ethylsulfanyl)ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —SO$_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl $C_3$-$C_8$-cycloalkyl," "$C_1$-$C_6$ alkyl heterocycloalkyl," "acyl", "amino," "amide", "aminosulfonyl," "ammonium," "acyl amino," "aminocarbonyl," "aryl," "heteroaryl," "sulfinyl," "sulfonyl," "sulphonamide", "alkoxy," "alkoxy carbonyl," "carbamate," "sulfanyl," "halogen," trihalomethyl, cyano, hydroxy, mercapto, nitro, and the like.

In a particular embodiment, the term optionally substituted "$C_1$-$C_6$ alkyl" includes optionally substituted halogenated "$C_1$-$C_6$ alkyl" such as fluorinated "$C_1$-$C_6$ alkyl" (e.g. —CF$_3$, —CF$_3$CH$_2$ or —CF$_3$CF$_2$).

The term "pharmaceutically acceptable salts or complexes" refers to salts or complexes of the compounds according to the invention. Examples of such salts include, but are not restricted, to base addition salts formed by reaction of aminopyridine derivatives of the invention with organic or inorganic bases such as hydroxide, carbonate or bicarbonate of a metal cation such as those selected in the group consisting of alkali metals (sodium, potassium or lithium), alkaline earth metals (e.g. calcium or magnesium).

Are also comprised salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein.

The term "indirectly" also encompasses prodrugs which may be converted to the active form of the drug via endogenous enzymes or metabolism. The prodrug is a derivative of the compounds according to the invention and presenting anti-malarial activity that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g. by oxidation, reduction, hydrolysis or the like, each of which is carried out enzymatically. These compounds can be produced from compounds of the present invention according to well-known methods.

The term "indirectly" also encompasses metabolites of compounds according to the invention.

The term "metabolite" refers to all molecules derived from any of the compounds according to the present invention in a cell or organism, preferably mammal.

The term "malaria" includes disease and conditions related to an infection by Plasmodium.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive phophylaxis is used whereas against *P. vivax* or a combination of *P. falciparum* and *P. vivax*, terminal prophylaxis is used.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like.

Compounds

The aminopyridine derivatives used in the manufacture of a medicament for the prevention or treatment of malaria, are capable of killing and/or inhibiting malaria parasite replication.

In a particular embodiment is provided an aminopyridine selected from the following group:

3-(6-Methoxypyridin-3-yl)-5-(4-methylsulfonylphenyl)pyridin-2-amine;

5-(4-methylsulfonylphenyl)-3-[3-(trifluoromethyl)phenyl]pyridin-2-amine;

3-[2-amino-5-(4-methylsulfonylphenyl)pyridin-3-yl]phenol;

4-[2-amino-5-(4-methylsulfonylphenyl)pyridin-3-yl]-2-methoxyphenol;

4-[2-amino-5-(6-methoxypyridin-3-yl)pyridin-3-yl]-2-methoxyphenol;

4-[6-amino-5-[4-(4-methylpiperazin-1-yl)phenyl]pyridin-3-yl]-2,6-dimethylphenol;

[4-[6-amino-5-(6-methoxypyridin-3-yl)pyridin-3-yl]phenyl]methanol; and

4-[6-amino-5-[4-(4-methylpiperazin-1-yl)phenyl]pyridin-3-yl]phenol; as well as tautomers, geometrical isomers, optically active forms, pharmaceutically acceptable salts or complexes and pharmaceutically active derivative thereof.

In another particular embodiment is provided an aminopyridine selected from the following group:

3-(6-Methoxypyridin-3-yl)-5-(4-methylsulfonylphenyl)pyridin-2-amine;

5-(4-methylsulfonylphenyl)-3-[3-(trifluoromethyl)phenyl]pyridin-2-amine;

3-[2-amino-5-(4-methylsulfonylphenyl)pyridin-3-yl]phenol;

4-[2-amino-5-(4-methylsulfonylphenyl)pyridin-3-yl]-2-methoxyphenol;

4-[2-amino-5-(6-methoxypyridin-3-yl)pyridin-3-yl]-2-methoxyphenol;

4-[6-amino-5-[4-(4-methylpiperazin-1-yl)phenyl]pyridin-3-yl]-2,6-dimethylphenol;

[4-[6-amino-5-(6-methoxypyridin-3-yl)pyridin-3-yl]phenyl]methanol; and

4-[6-amino-5-[4-(4-methylpiperazin-1-yl)phenyl]pyridin-3-yl]phenol;

(N,N-dimethyl) {4-[2-amino-3-(2-methoxypyridin-5-yl)pyridin-5-yl]benzene}sulphonamide;
4-[2-amino-3-(2-methoxypyridin-5-yl)pyridin-5-yl]-N,N-dimethyl benzamide;
5-(2-methoxy pyridin-5-yl)-3-[4-(methylsulfonyl) phenyl]pyridin-2-amine;
5-[4-(methyl sulfonyl)phenyl]-3-(pyrimidin-5-yl)pyridin-2-amine;
(Morpholino) {4-[2-amino-3-(2-methoxypyridin-5-yl)pyridin-5-yl]benzene}sulphonamide;
(N-methyl piperazin) {4-[2-amino-3-(2-methoxypyridin-5-yl)pyridin-5-yl]benzene}sulphonamide;
3,5-di-[4-(methylsulfonyl)phenyl]pyridin-2-amine;
3-(2-methoxy pyridin-5-yl)-5-[3-(methyl sulfonyl)phenyl]pyridin-2-amine;
(N-methyl) {4-[2-amino-3-(2-methoxypyridin-5-yl)pyridin-5-yl]benzene}sulphonamide;
4-[2-amino-3-(2-methoxypyridin-5-yl)pyridin-5-yl]-N-methylbenzamide;
{4-[2-amino-3-(2-methoxy pyridin-5-yl) pyridin-5-yl]phenyl}(morpholino)methanone;
4-[2-amino-3-(2-methoxypyridin-5-yl)pyridin-5-yl]benzamide;
4-[6-amino-5-(2-methoxypyridin-5-yl)pyridin-3-yl]benzoic acid;
N-{4-[2-amino-3-(2-methoxy pyridin-5-yl) pyridin-5-yl]benzene}methyl sulphonamide;
4-[6-amino-5-(6-methoxypyridin-3-yl)pyridin-3-yl]-N-(3-hydroxypropyl)benzamide;
5-(benzo[c][1,2,5]oxadiazol-6-yl)-3-(2-methoxypyridin-5-yl)pyridin-2-amine;
N-cyclopropyl-{4-[2-amino-3-(2-methoxy pyridin-5-yl) pyridin-5-yl]benzene}sulphonamide;
5-(H-imidazo[1,2-a]pyridin-6-yl)-3-(2-methoxy pyridin-5-yl)pyridin-2-amine;
3-(2-methoxy pyridin-5-yl)-5-(1-methyl-1H-indazol-6-yl)pyridin-2-amine;
4-[2-amino-3-(2-methoxypyridin-5-yl)pyridin-5-yl]-N-cyclopropyl benzamide;
4-[2-amino-3-(2-methoxypyridin-5-yl)pyridin-5-yl]-N-(2-morpholino ethyl)benzamide;
3-[2-amino-3-(2-methoxypyridin-5-yl)pyridin-5-yl]benzamide;
3-(2-methoxypyridin-5-yl)-5-[4-(5-methyl-1,3,4-oxadiazol-2-yl)phenyl]pyridin-2-amine;
3-(2-methoxypyridin-5-yl)-5-(6-morpholinopyridin-3-yl)pyridin-2-amine;
5-[4-(1H-pyrazol-1-yl)phenyl]-3-(2-methoxy pyridin-5-yl)pyridin-2-amine;
3-(2-methoxy pyridin-5-yl)-5-(quinolin-6-yl) pyridin-2-amine;
4-[2-amino-3-(2-methoxypyridin-5-yl)pyridin-5-yl]-N-[2-(pyrrolidin-1-yl)ethyl]benzamide;
5-[2-(trifluoro methyl)-4-(methylsulfonyl)phenyl]-3-(2-methoxypyridin-5-yl)pyridin-2-amine;
{4-[2-amino-3-(4-carbamoyl phenyl)pyridin-5-yl]phenyl}(morpholino)methanone;
4-[2-amino-3-(2-methylpyridin-5-yl)pyridin-5-yl]benzamide;
4-[2-amino-5-[4-(4-morpholinylcarbonyl)phenyl]-pyridin-3yl]-N-(2-hydroxyethyl)-benzamide;
4-[2-amino-3-(2-methoxypyridin-5-yl)pyridin-5-yl]benzene sulphonamide;
4-[2-amino-3-(4-benzamido)pyridin-5-yl]benzamide;
{4-[2-amino-3-(2-methoxypyridin-5-yl)pyridin-5-yl]phenyl}(4-methylpiperazin-1-yl) methanone;
4-[2-amino-3-(2-methoxypyridin-5-yl)pyridin-5-yl]-N-[4-(aminomethyl)thiazol-2-yl]benzamide;
{4-[2-amino-3-(4-(trifluoromethyl)phenyl)pyridin-5-yl]phenyl}(morpholino)methanone;
3-(2-methoxy pyridin-3-yl)-5-[4-(methyl sulfonyl phenyl]pyridin-2-amine;
5-[4-(methyl sulfonyl)phenyl]-3-(pyridin-3-yl)pyridin-2-amine;
4-{2-amino-5-[4-(methylsulfonyl)phenyl]pyridin-3-yl}benzonitrile;
3-{2-amino-5-[4-(methylsulfonyl)phenyl]pyridin-3-yl}benzonitrile;
4-{2-amino-5-[4-(methylsulfonyl)phenyl]pyridin-3-yl}benzamide;
4-{2-amino-5-[4-(methylsulfonyl)phenyl]pyridin-3-yl}-N-methylbenzamide;
3-(H-imidazo [1,2-a]pyridin-6-yl)-5-[4-(methyl sulfonyl)phenyl]pyridin-2-amine;
3-(2-methoxy pyrimidin-5-yl)-5-[4-(methylsulfonyl)phenyl]pyridin-2-amine;
5-[4-(methyl sulfonyl)phenyl]-3-(quinoxalin-7-yl)pyridin-2-amine;
3-(furan-3-yl)-5-[4-(methylsulfonyl)phenyl]pyridin-2-amine;
3-[4-(5-methyl-1,3,4-oxadiazol-2-yl)phenyl]-5-[4-(methylsulfonyl)phenyl]pyridin-2-amine;
3-(3-chloro-2-methoxypyridin-5-yl)-5-[4-(methylsulfonyl)phenyl]pyridin-2-amine;
5-[4-(methylsulfonyl)phenyl]-3-[3-(trifluoromethoxy)phenyl]pyridin-2-amine;
5-[4-(methylsulfonyl)phenyl]-3-[4-(trifluoromethoxy)phenyl]pyridin-2-amine;
5-[4-(methylsulfonyl)phenyl]-3-[2-(pyrrolidin-1-yl)pyridin-5-yl]pyridin-2-amine;
3-[2-chloro-4-(trifluoromethyl)phenyl]-5-[4-(methylsulfonyl)phenyl]pyridin-2-amine;
3-(3-methoxy pyridin-4-yl)-5-[4-(methylsulfonyl)phenyl]pyridin-2-amine;
5-[4-(methylsulfonyl)phenyl]-3-(2-morpholino pyridin-5-yl)pyridin-2-amine;
3-[2-(trifluoromethyl)pyridin-4-yl]-5-[4-(methylsulfonyl)phenyl]pyridin-2-amine;
3-(2-methylpyridin-5-yl)-5-[4-(methyl sulfonyl)phenyl]pyridin-2-amine;
3-[2-(trifluoro methyl)pyridin-5-yl]-5-[4-(methyl sulfonyl)phenyl]pyridin-2-amine;
3-{4-[2-(pyrrolidin-1-yl)ethoxy]phenyl}-5-[4-(methylsulfonyl)phenyl]pyridin-2-amine;
5-[4-(methyl sulfonyl)phenyl]-3-(4-morpholinophenyl)pyridin-2-amine;
3-[4-(1H-pyrazol-1-yl)phenyl]-5-[4-(methylsulfonyl)phenyl]pyridin-2-amine;
5-{2-amino-5-[4-(methylsulfonyl)phenyl]pyridin-3-yl}pyrimidin-2-amine;
3-{2-amino-5-[4-(methylsulfonyl)phenyl]pyridin-3-yl}benzamide;
3-(6-methoxy-2-methylpyridin-3-yl)-5-[4-(methylsulfonyl)phenyl]pyridin-2-amine;
3-(isoquinolin-5-yl)-5-[4-(methyl sulfonyl)phenyl]pyridin-2-amine;
5-[4-(methyl sulfonyl)phenyl]-3-(quinolin-6-yl)pyridin-2-amine;
5-[4-(methylsulfonyl)phenyl]-3-p-tolylpyridin-2-amine;
{5-[2-amino-5-(4-(methylsulfonyl)phenyl)pyridin-3-yl]pyridin-2-yl}methanol;
3-(2-methylbenzo[d]thiazol-5-yl)-5-[4-(methylsulfonyl)phenyl]pyridin-2-amine;

N-{4-[2-amino-5-(4-(methylsulfonyl) phenyl)pyridin-3-yl]phenyl}-2-(dimethylamino) acetamide;

3-(2-fluoropyridin-5-yl)-5-[4-(methylsulfonyl)phenyl]pyridin-2-amine;

5-[4-(methylsulfonyl)phenyl]-3-[2-(methylsulfonyl)pyridin-5-yl]pyridin-2-amine;

N-{5-[2-amino-5-(4-(methylsulfonyl)phenyl)pyridin-3-yl]pyridin-2-yl}acetamide;

3-(benzo[c][1,2,5]oxadiazol-5-yl)-5-[4-(methylsulfonyl)phenyl]pyridin-2-amine;

3-{2-amino-5-[4-(methylsulfonyl)phenyl]pyridin-3-yl]-N-(2-hydroxyethyl)benzamide;

3-[4-(trifluoromethyl)phenyl]-5-[4-(methylsulfonyl)phenyl]pyridin-2-amine;

3-(3-methylpyridin-5-yl)-5-[4-(methylsulfonyl)phenyl]pyridin-2-amine; and

5-[3-fluoro-4-(methylsulfonyl)phenyl]-3-(2-methoxypyridin-5-yl)pyridin-2-amine.

Compositions

The invention provides pharmaceutical compositions useful for the prophylaxis or treatment of malaria. The invention further provides methods for treating a mammalian patient, and most preferably a human patient, who is suffering from malaria.

In another particular embodiment, is provided a pharmaceutical formulation containing at least one derivative according the invention and a pharmaceutically acceptable carrier, diluent or excipient thereof.

In another particular embodiment, is provided a pharmaceutical formulation comprising an aminopyridine according to Formula (I) and an antimalarial agent, wherein X and Y are as defined in the detailed description.

Pharmaceutical compositions of the invention can contain one or more compound(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. Compositions according to the invention are preferably oral. Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences*, 21$^{st}$ Edition, 2005, University of the Sciences in Philadelphia, Lippincott Williams & Wilkins, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of administration

Compositions of this invention may be administered in any manner, including, but not limited to, orally, parenterally, sublingually, transdermally, vaginally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular.

The compositions of this invention may also be administered in the form of an implant, which allows slow release of the compositions as well as a slow controlled i.v. infusion. In a preferred embodiment, aminopyridine derivatives according to the invention are administered orally.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to the invention, the aminopyridine derivatives of the invention and pharmaceutical formulations thereof can be administered alone or in combination with a co-agent useful in the treatment of malaria, such as substances useful in the treatment and/or prevention of malaria e.g. for example a co-agent including, but not limited to, artemether, chloroquine, mefloquine, quinine, atovaquone/proguanil, doxycycline, hydroxychloroquine, halofantrine, pyrimethamine-sulfadoxine and piperaquine.

The invention encompasses the administration of an aminopyridine derivative according to the invention or of a pharmaceutical formulation thereof, wherein the aminopyridine derivative or the pharmaceutical formulation thereof is administered to an individual prior to, simultaneously or sequentially with other therapeutic regimens or co-agents useful in the treatment of malaria (e.g. multiple drug regimens), in an effective amount. Aminopyridine derivatives or the pharmaceutical formulations thereof that are administered simultaneously with said co-agents can be administered in the same or different composition(s) and by the same or different route(s) of administration.

Patients

In an embodiment, patients according to the invention are patients suffering from malaria.

In another embodiment, patients according to the invention are patients with a high risk of being infected by *Plasmodium*.

Use according to the Invention

In one embodiment, the invention provides a use of an aminopyridine derivative according to Formula (I),

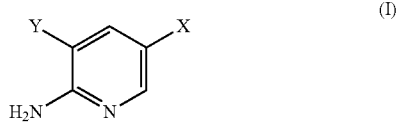

(I)

wherein X and Y are independently selected from optionally substituted aryl and optionally substituted heteroaryl, as well as tautomers, geometrical isomers, optically active forms, pharmaceutically acceptable salts or complexes and pharmaceutically active derivative thereof for the preparation of a pharmaceutical composition for the treatment or prophylaxis of malaria.

In a further embodiment, the invention provides a use according to the invention, wherein X is an optionally substituted aryl such as optionally substituted phenyl (e.g. optionally substituted sulphonyl phenyl like 4-methyl sulphonyl phenyl, 2,6 methyl phenol, 4-methanol phenyl, phenol, 5-methyl-1,3,4-oxadiazol-2-yl phenyl, 1H-pyrazol-1-yl phenyl).

In a further embodiment, the invention provides a use according to the invention, wherein X is an optionally substituted phenyl selected from optionally substituted sulphonyl phenyl such as optionally substituted $C_1$-$C_6$ alkyl sulfonyl phenyl (e.g. 4-methyl sulfonyl phenyl, 3-methyl sulfonyl phenyl, 3-fluoro-4-methyl sulfonyl phenyl), optionally substituted sulphonamide phenyl (e.g. N,N-dimethyl benzene sulphonamide, morpholino benzene sulphonamide, N-methyl piperazine benzene sulphonamide, N-cyclopropyl benzene sulphonamide, N-methyl benzene sulfonamide, benzene sulfonamide), optionally substituted phenyl amide (e.g. N,N-dimethyl benzamide, N-methyl benzamide, N-cyclopropyl benzyl amide, 2-morpholinoethyl benzamide, benzamide, ethyl benzamide, 4-(aminomethyl)thiazol-2-yl benzamide, 3-hydroxypropyl benzamide), optionally substituted amino sulfonyl phenyl (e.g. methyl sulfonamide phenyl) and optionally substituted carbonyl phenyl (e.g. morpholino methanone phenyl, benzoic acid, 4-methylpiperazon-1-yl methanone).

In another further embodiment, the invention provides a use according to the invention, wherein X is an optionally substituted heteroaryl such as optionally substituted pyridine (e.g. 6-methoxy pyridin-3-yl, 2-methoxy pyridine-5-yl, 6-morpholinopyridin-3yl) and optionally substituted pyrazole.

In another further embodiment, the invention provides a use according to the invention, wherein X is selected from optionally substituted benzo[c][1,2,5]oxadiazolyl (e.g. benzo [c][1,2,5]oxadiazol-6-yl), optionally substituted indazolyl (e.g. 1-methyl-1H-indazol-6-yl), optionally substituted quinolinyl (e.g. quinolin-6-yl), optionally substituted imidazolyl (e.g. 5-H-imidazo[1,2,a]-6-yl).

In another further embodiment, the invention provides a use according to the invention, wherein X is optionally substituted imidazolyl (e.g. 5-H-imidazo[1,2, a]-6-yl).

In a further embodiment, the invention provides a use according to the invention, wherein Y is an optionally substituted aryl such as optionally substituted phenyl (e.g. 3-trifluoro methyl phenyl, phenol, 2-methoxy phenol, 4-methylpiperazin-1-yl phenyl, optionally substituted sulphonyl phenyl, 4-cyano phenyl, 3-cyanophenyl, 3-trifluoromethoxy phenyl, 4-trifluoromethoxy phenyl, 2-chloro-4-trifluoromethyl phenyl, 2-pyrrolidin-1-yl ethoxy phenyl, 4-morpholino phenyl, 1H-pyrazol-1-yl phenyl, p-tolyl, 4-trifluoromethyl phenyl).

In a further embodiment, the invention provides a use according to the invention, wherein Y is an optionally substituted phenyl selected from optionally substituted cyano phenyl, optionally substituted methoxy phenyl (e.g. 3-trifluoromethoxy phenyl, 4-trifluoromethoxy phenyl), optionally substituted heteroaryl phenyl (e.g. 1H-pyrazol-1-yl phenyl), optionally substituted $C_1$-$C_6$ alkyl phenyl (e.g. p-tolyl, 4-trifluoromethyl phenyl), optionally substituted sulphonyl phenyl such as optionally substituted $C_1$-$C_6$ alkyl sulfonyl phenyl (e.g. 4-methyl sulfonyl phenyl), and optionally substituted phenyl amide (e.g. 2-amino benzamide, N-methyl benzamide, 2-hydroxyethyl benzamide, benzamide, 2-dimethylamino acetamide phenyl, 2-hydroxyethyl benzamide).

In another further embodiment, the invention provides a use according to the invention, wherein Y is an optionally substituted heteroaryl such as optionally substituted pyridine (e.g. pyridine-3-yl, 2-methoxypyridin-3-yl, 2-methoxypyridin-5-yl, 3-methoxypyridin-4-yl, 6-methoxy-2-methylpyridin-3-yl, 2-methyl pyridine-5-yl, 3-methylpyridin-5-yl, 2-trifluoromethyl pyridin-5-yl, 2-trifluoromethyl pyridine-4-y 1, 2-fluoropyridin-5-yl, pyridine-2-yl methanol, 3-chloro-2-methoxypyridin-5-yl, 2-pyrrolidin-1-yl pyridine-5-yl, 2-morpholinopyridin-5-yl, 2-methyl sulfonyl pyridine-5-yl, pyridine-2-yl acetamnide), optionally substituted pyrimidine (e.g. 2-methoxypyrididin-5-yl, pyrimidin-2-amine) and optionally substituted pyrazole.

In another further embodiment, the invention provides a use according to the invention, wherein Y is an optionally substituted heteroaryl such as optionally substituted pyridine (e.g. pyridine-3-yl, 2-methoxypyridin-3-yl, 2-methoxypyridin-5-yl, 3-methoxypyridin-4-yl, 6-methoxy-2-methylpyridin-3-yl, 2-methyl pyridine-5-y 1, 3-methylpyridin-5-yl, 2-trifluoromethyl pyridin-5-yl, 2-trifluoromethyl pyridine-4-yl, 2-fluoropyridin-5-yl, pyridine-2-yl methanol, 3-chloro-2-methoxypyridin-5-yl, 2-pyrrolidin-1-yl pyridine-5-yl, 2-morpholinopyridin-5-yl, 2-methyl sulfonyl pyridine-5-yl, pyridine-2-yl acetamnide), optionally substituted pyrimidine (e.g. 2-methoxypyrididin-5-yl, pyrimidin-2-amine), optionally substituted furanyl (e.g. furan-3-yl), optionally substituted quinoxalin (e.g. 3-quinoxalin-7-yl), optionally substituted imidazolyl (e.g. 3-H-imidazo[1,2,a]-6-yl), optionally substituted isoquinolinyl (e.g. isoquinolin-5-yl), optionally substituted quinolinyl (e.g. 3-quinolin-6-yl) optionally substituted benzothiazolyl (e.g. 2-methylbenzo [d]thiazol-5-yl) and optionally substituted benzoxadiazolyl (e.g. 3-benzo[c][1,2,5]oxadiazol-5-yl) optionally substituted pyrazole.

In another further embodiment, the invention provides a use according to the invention, wherein Y is an optionally substituted pyridine.

In another further embodiment, the invention provides a use according to the invention, wherein Y is an optionally substituted pyrimidine.

In another further embodiment, the invention provides a use according to the invention, wherein Y is an optionally substituted quinolinyl.

In another further embodiment, the invention provides a use according to the invention, wherein X is an optionally substituted phenyl selected from optionally substituted sulphonyl phenyl such as optionally substituted $C_1$-$C_6$ alkyl sulfonyl, optionally substituted sulphonamide phenyl, optionally substituted phenyl amide and optionally substituted carbonyl phenyl and Y is an optionally substituted pyridine.

In another further embodiment, the invention provides a use according to the invention, wherein X is an optionally substituted phenyl selected from optionally substituted sulphonyl phenyl such as optionally substituted $C_1$-$C_6$ alkyl sulfonyl phenyl, optionally substituted sulphonamide phenyl, optionally substituted phenyl amide and optionally substituted carbonyl phenyl and Y is an optionally substituted phenyl selected from optionally substituted cyano phenyl, optionally substituted methoxy phenyl, optionally substituted heteroaryl phenyl, optionally substituted $C_1$-$C_6$ alkyl phenyl, optionally substituted sulphonyl phenyl such as optionally substituted $C_1$-$C_6$ alkyl sulfonyl phenyl, and optionally substituted phenyl amide.

In another further embodiment, the invention provides a use according to the invention, wherein X is an optionally substituted phenyl selected from optionally substituted sulphonyl phenyl such as optionally substituted $C_1$-$C_6$ alkyl sulfonyl phenyl, optionally substituted sulphonamide phenyl, optionally substituted phenyl and optionally substituted carbonyl phenyl and Y is an optionally substituted pyrimidine.

In another further embodiment, the invention provides a use according to the invention, wherein X is an optionally substituted phenyl selected from optionally substituted sulphonyl phenyl such as optionally substituted $C_1$-$C_6$ alkyl sulfonyl phenyl, optionally substituted sulphonamide phenyl, optionally substituted phenyl and optionally substituted carbonyl phenyl and Y is an optionally substituted quinolinyl.

In another further embodiment, the invention provides a use according to the invention, wherein X is an optionally substituted imidazolyl and Y is an optionally substituted pyridine.

In a particular embodiment, aminopyridine derivatives of the invention include in particular those selected from the following group:
3-(6-Methoxypyridin-3-yl)-5-(4-methylsulfonylphenyl)pyridin-2-amine;
5-(4-methylsulfonylphenyl)-3-[3-(trifluoromethyl)phenyl]pyridin-2-amine;
3-[2-amino-5-(4-methylsulfonylphenyl)pyridin-3-yl]phenol;
4-[2-amino-5-(4-methylsulfonylphenyl)pyridin-3-yl]-2-methoxyphenol;
4-[2-amino-5-(4-methylsulfonylphenyl)pyridin-3-yl]phenol;
4-[2-amino-5-(6-methoxypyridin-3-yl)pyridin-3-yl]-2-methoxyphenol;
4-[6-amino-5-[4-(4-methylpiperazin-1-yl)phenyl]pyridin-3-yl]-2,6-dimethylphenol;
[4-[6-amino-5-(6-methoxypyridin-3-yl)pyridin-3-yl]phenyl]methanol; and
4-[6-amino-5-[4-(4-methylpiperazin-1-yl)phenyl]pyridin-3-yl]phenol.

In another particular embodiment, aminopyridine derivatives of the invention include in particular those selected from the following group:
3-(6-Methoxypyridin-3-yl)-5-(4-methylsulfonylphenyl)pyridin-2-amine;
5-(4-methylsulfonylphenyl)-3-[3-(trifluoromethyl)phenyl]pyridin-2-amine;
3-[2-amino-5-(4-methylsulfonylphenyl)pyridin-3-yl]phenol;
4-[2-amino-5-(4-methylsulfonylphenyl)pyridin-3-yl]-2-methoxyphenol;
4-[2-amino-5-(4-methylsulfonylphenyl)pyridin-3-yl]phenol;
4-[2-amino-5-(6-methoxypyridin-3-yl)pyridin-3-yl]-2-methoxyphenol;
4-[6-amino-5-[4-(4-methylpiperazin-1-yl)phenyl]pyridin-3-yl]-2,6-dimethylphenol;
[4-[6-amino-5-(6-methoxypyridin-3-yl)pyridin-3-yl]phenyl]methanol;
4-[6-amino-5-[4-(4-methylpiperazin-1-yl)phenyl]pyridin-3-yl]phenol;
(N,N-dimethyl) {4-[2-amino-3-(2-methoxypyridin-5-yl)pyridin-5-yl]benzene}sulphonamide;
4-[2-amino-3-(2-methoxypyridin-5-yl)pyridin-5-yl]-N,N-dimethyl benzamide;
5-(2-methoxy pyridin-5-yl)-3-[4-(methylsulfonyl) phenyl] pyridin-2-amine;
5-[4-(methyl sulfonyl)phenyl]-3-(pyrimidin-5-yl)pyridin-2-amine;
(Morpholino) {4-[2-amino-3-(2-methoxypyridin-5-yl)pyridin-5-yl]benzene}sulphonamide;
3,5-di(2-methoxypyridin-5-yl)pyridin-2-amine;

(N-methyl piperazin) {4-[2-amino-3-(2-methoxypyridin-5-yl)pyridin-5-yl]benzene}sulphonamide;
3,5-di-[4-(methylsulfonyl)phenyl]pyridin-2-amine;
3-(2-methoxy pyridin-5-yl)-5-[3-(methyl sulfonyl)phenyl]pyridin-2-amine;
(N-methyl) {4-[2-amino-3-(2-methoxypyridin-5-yl)pyridin-5-yl]benzene}sulphonamide;
4-[2-amino-3-(2-methoxypyridin-5-yl)pyridin-5-yl]-N-methylbenzamide;
{4-[2-amino-3-(2-methoxy pyridin-5-yl) pyridin-5-yl]phenyl}(morpholino)methanone;
4-[2-amino-3-(2-methoxypyridin-5-yl)pyridin-5-yl]benzamide;
4-[6-amino-5-(2-methoxypyridin-5-yl)pyridin-3-yl]benzoic acid;
N-{4-[2-amino-3-(2-methoxy pyridin-5-yl) pyridin-5-yl]benzene}methyl sulphonamide;
4-[6-amino-5-(6-methoxypyridin-3-yl)pyridin-3-yl]-N-(3-hydroxypropyl)benzamide;
5-(benzo[c][1,2,5]oxadiazol-6-yl)-3-(2-methoxypyridin-5-yl)pyridin-2-amine;
N-cyclopropyl-{4-[2-amino-3-(2-methoxy pyridin-5-yl) pyridin-5-yl]benzene}sulphonamide;
5-(H-imidazo[1,2-a]pyridin-6-yl)-3-(2-methoxy pyridin-5-yl)pyridin-2-amine;
3-(2-methoxy pyridin-5-yl)-5-(1-methyl-1H-indazol-6-yl) pyridin-2-amine;
4-[2-amino-3-(2-methoxypyridin-5-yl)pyridin-5-yl]-N-cyclopropyl benzamide;
4-[2-amino-3-(2-methoxypyridin-5-yl)pyridin-5-yl]-N-(2-morpholino ethyl)benzamide;
3-[2-amino-3-(2-methoxypyridin-5-yl)pyridin-5-yl]benzamide;
3-(2-methoxypyridin-5-yl)-5-[4-(5-methyl-1,3,4-oxadiazol-2-yl)phenyl]pyridin-2-amine;
3-(2-methoxypyridin-5-yl)-5-(6-morpholinopyridin-3-yl) pyridin-2-amine;
5-[4-(1H-pyrazol-1-yl)phenyl]-3-(2-methoxy pyridin-5-yl) pyridin-2-amine;
3-(2-methoxy pyridin-5-yl)-5-(quinolin-6-yl) pyridin-2-amine;
4-[2-amino-3-(2-methoxypyridin-5-yl)pyridin-5-yl]-N-[2-(pyrrolidin-1-yl)ethyl]benzamide;
5-[2-(trifluoro methyl)-4-(methylsulfonyl)phenyl]-3-(2-methoxypyridin-5-yl)pyridin-2-amine;
{4-[2-amino-3-(4-carbamoyl phenyl)pyridin-5-yl]phenyl}(morpholino)methanone;
4-[2-amino-3-(2-methylpyridin-5-yl)pyridin-5-yl]benzamide;
4-[2-amino-5-[4-(4-morpholinylcarbonyl)phenyl]-pyridin-3yl]-N-(2-hydroxyethyl)-benzamide;
4-[2-amino-3-(2-methoxypyridin-5-yl)pyridin-5-yl]benzene sulphonamide;
4-[2-amino-3-(4-benzamido)pyridin-5-yl]benzamide;
{4-[2-amino-3-(2-methoxypyridin-5-yl)pyridin-5-yl]phenyl}(4-methylpiperazin-1-yl) methanone;
4-[2-amino-3-(2-methoxypyridin-5-yl)pyridin-5-yl]-N-[4-(aminomethyl)thiazol-2-yl]benzamide;
{4-[2-amino-3-(4-(trifluoromethyl)phenyl)pyridin-5-yl]phenyl}(morpholino)methanone;
3-(2-methoxy pyridin-3-yl)-5-[4-(methyl sulfonyl phenyl]pyridin-2-amine;
5-[4-(methyl sulfonyl)phenyl]-3-(pyridin-3-yl)pyridin-2-amine;
4-{2-amino-5-[4-(methylsulfonyl)phenyl]pyridin-3-yl}benzonitrile;
3-{2-amino-5-[4-(methylsulfonyl)phenyl]pyridin-3-yl}benzonitrile;
4-{2-amino-5-[4-(methylsulfonyl)phenyl]pyridin-3-yl}benzamide;
4-{2-amino-5-[4-(methylsulfonyl)phenyl]pyridin-3-yl}-N-methylbenzamide;
3-(H-imidazo[1,2-a]pyridin-6-yl)-5-[4-(methyl sulfonyl) phenyl]pyridin-2-amine;
3-(2-methoxy pyrimidin-5-yl)-5-[4-(methylsulfonyl)phenyl] pyridin-2-amine;
5-[4-(methyl sulfonyl)phenyl]-3-(quinoxalin-7-yl)pyridin-2-amine;
3-(furan-3-yl)-5-[4-(methylsulfonyl)phenyl]pyridin-2-amine;
3-[4-(5-methyl-1,3,4-oxadiazol-2-yl)phenyl]-5-[4-(methylsulfonyl)phenyl]pyridin-2-amine;
3-(3-chloro-2-methoxypyridin-5-yl)-5-[4-(methylsulfonyl) phenyl]pyridin-2-amine;
5-[4-(methylsulfonyl)phenyl]-3-[3-(trifluoromethoxy)phenyl]pyridin-2-amine;
5-[4-(methylsulfonyl)phenyl]-3-[4-(trifluoromethoxy)phenyl]pyridin-2-amine;
5-[4-(methylsulfonyl)phenyl]-3-[2-(pyrrolidin-1-yl)pyridin-5-yl]pyridin-2-amine;
3-[2-chloro-4-(trifluoromethyl)phenyl]-5-[4-(methylsulfonyl) phenyl]pyridin-2-amine;
3-(3-methoxy pyridin-4-yl)-5-[4-(methylsulfonyl)phenyl] pyridin-2-amine;
5-[4-(methylsulfonyl)phenyl]-3-(2-morpholino pyridin-5-yl)pyridin-2-amine;
3-[2-(trifluoromethyl)pyridin-4-yl]-5-[4-(methylsulfonyl) phenyl]pyridin-2-amine;
3-(2-methylpyridin-5-yl)-5-[4-(methyl sulfonyl)phenyl]pyridin-2-amine;
3-[2-(trifluoro methyl)pyridin-5-yl]-5-[4-(methyl sulfonyl) phenyl]pyridin-2-amine;
3-{4-[2-(pyrrolidin-1-yl)ethoxy]phenyl}-5-[4-(methylsulfonyl)phenyl]pyridin-2-amine;
5-[4-(methyl sulfonyl)phenyl]-3-(4-morpholinophenyl)pyridin-2-amine;
3-[4-(1H-pyrazol-1-yl)phenyl]-5-[4-(methylsulfonyl)phenyl]pyridin-2-amine;
5-{2-amino-5-[4-(methylsulfonyl)phenyl]pyridin-3-yl}pyrimidin-2-amine;
3-{2-amino-5-[4-(methylsulfonyl)phenyl]pyridin-3-yl}benzamide;
3-(6-methoxy-2-methylpyridin-3-yl)-5-[4-(methylsulfonyl) phenyl]pyridin-2-amine;
3-(isoquinolin-5-yl)-5-[4-(methyl sulfonyl)phenyl]pyridin-2-amine;
5-[4-(methyl sulfonyl)phenyl]-3-(quinolin-6-yl)pyridin-2-amine;
5-[4-(methylsulfonyl)phenyl]-3-p-tolylpyridin-2-amine;
{5-[2-amino-5-(4-(methylsulfonyl)phenyl)pyridin-3-yl]pyridin-2-yl}methanol;
3-(2-methylbenzo[d]thiazol-5-yl)-5-[4-(methylsulfonyl) phenyl]pyridin-2-amine;
N-{4-[2-amino-5-(4-(methylsulfonyl) phenyl)pyridin-3-yl] phenyl}-2-(dimethylamino) acetamide;
3-(2-fluoropyridin-5-yl)-5-[4-(methylsulfonyl)phenyl]pyridin-2-amine;
5-[4-(methylsulfonyl)phenyl]-3-[2-(methylsulfonyl)pyridin-5-yl]pyridin-2-amine;
N-{5-[2-amino-5-(4-(methylsulfonyl)phenyl)pyridin-3-yl] pyridin-2-yl}acetamide;
3-(benzo[c][1,2,5]oxadiazol-5-yl)-5-[4-(methylsulfonyl) phenyl]pyridin-2-amine;

3-{2-amino-5-[4-(methylsulfonyl)phenyl]pyridin-3-yl]-N-(2-hydroxyethyl)benzamide;
3-[4-(trifluoromethyl)phenyl]-5-[4-(methylsulfonyl)phenyl]pyridin-2-amine;
3-(3-methylpyridin-5-yl)-5-[4-(methylsulfonyl)phenyl]pyridin-2-amine; and
5-[3-fluoro-4-(methylsulfonyl)phenyl]-3-(2-methoxypyridin-5-yl)pyridin-2-amine.

In another particular embodiment, is provided an aminopyridine according to the invention for use as a medicament with the proviso that it is not 4-[2-amino-5-(4-methylsulfonyl phenyl)pyridin-3-yl]phenol.

In another embodiment, the invention provides a method for preventing or treating malaria in a patient. The method comprises administering an effective amount of an aminopyridine derivative according to the invention, or a pharmaceutically acceptable salt or complex or a pharmaceutically active derivative thereof or a pharmaceutical formulation thereof in a patient in need thereof.

In another embodiment, the invention provides an aminopyridine derivative according to the invention as well as pharmaceutically acceptable salts or complexes and pharmaceutically active derivatives thereof, for use in the treatment or prophylaxis of malaria.

In another embodiment, the invention provides a use of an aminopyridine derivative or a method according to the invention wherein the aminopyridine derivative is to be administered in combination with a co-agent useful in the treatment of malaria.

In another embodiment, the invention provides a pharmaceutical composition comprising an aminopyridine derivative according to the invention in combination with a co-agent useful in the treatment of malaria.

In another embodiment, the invention provides a process for the preparation of an aminopyridine derivative according to the invention comprising the step of reacting a substituted 5-bromopyridin-2-amine derivative according to Formula (iv) with a boronic acid of Formula (v) under Suzuki reaction conditions to lead to a compound of Formula (I):

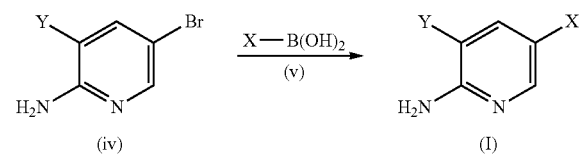

wherein X and Y are as described herein.

In a further aspect according to the invention is provided a process according to the invention wherein the substituted 5-bromopyridin-2-amine derivative according to Formula (iv) wherein Y is as defined herein is selected from the group consisting of:
3-(2-amino-5-bromo-3-pyridyl)phenol;
4-(2-amino-5-bromo-3-pyridyl)-2-methoxy-phenol;
4-(2-amino-5-bromo-3-pyridyl)phenol;
4-(2-amino-5-bromo-3-pyridyl)-2-methoxy-phenol;
5-bromo-3-[4-(4-methylpiperazin-1-yl)phenyl]pyridin-2-amine;
5-bromo-6'-methoxy-3,3'-bipyridin-2-amine;
5-bromo-3-(4-(methylsulfonyl)phenyl)pyridin-2-amine;
5-bromo-3-(pyrimidin-5-yl)pyridin-2-amine;
5-bromo-6'-methyl-3,3'-bipyridin-2-amine;
4-(2-amino-5-bromopyridin-3-yl)-N-(2-hydroxyethyl)benzamide; and
5-bromo-3-(4-(trifluoromethyl)phenyl)pyridin-2-amine.

In another embodiment, the invention provides intermediates of Formula (iv) wherein Y is as defined herein selected from the following group:
3-(2-amino-5-bromo-3-pyridyl)phenol;
4-(2-amino-5-bromo-3-pyridyl)-2-methoxy-phenol;
4-(2-amino-5-bromo-3-pyridyl)phenol;
4-(2-amino-5-bromo-3-pyridyl)-2-methoxy-phenol;
5-bromo-3-[4-(4-methylpiperazin-1-yl)phenyl]pyridin-2-amine;
5-bromo-6'-methoxy-3,3'-bipyridin-2-amine;
5-bromo-3-(4-(methylsulfonyl)phenyl)pyridin-2-amine;
5-bromo-3-(pyrimidin-5-yl)pyridin-2-amine;
5-bromo-6'-methyl-3,3'-bipyridin-2-amine;
4-(2-amino-5-bromopyridin-3-yl)-N-(2-hydroxyethyl)benzamide; and
5-bromo-3-(4-(trifluoromethyl)phenyl)pyridin-2-amine.

In another embodiment, the invention provides an intermediate of Formula (viii) wherein X is as defined herein and where the intermediate is 3-bromo-5-(4-(methylsulfonyl)phenyl)pyridin-2-amine.

In another embodiment, the invention provides intermediates of Formula (iii) or (v) wherein X and Y are as defined where the intermediate 2-amino-6'-methoxy-3,3'-bipyridin-5-ylboronic acid.

Aminopyridines according to the present invention also comprise their tautomers, their geometrical isomers, their optically active forms as enantiomers, diastereomers and their racemate forms, as well as pharmaceutically acceptable salts, complexes, prodrugs and metabolites thereof.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

Synthesis of Compounds According to the Invention:

The aminopyridine derivatives can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures.

A general synthetic approach for obtaining compounds of Formula (I) is depicted in Scheme 1 below. Aminopyridine derivatives according to Formula (I), whereby the substituents X and Y are as above defined, may be prepared in 1-3 chemical steps, from custom made or commercially available 5-bromopyridin-2-amine according to Formula (i), 5-bromo-3-iodopyridin-2-amine according to Formula (ii), boronic acids of Formulae (iii) or (v), and substituted 5-bromopyridin-2-amine derivatives according to Formula (iv), following the synthetic pathway as outlined in Scheme 1 below.

Scheme 1

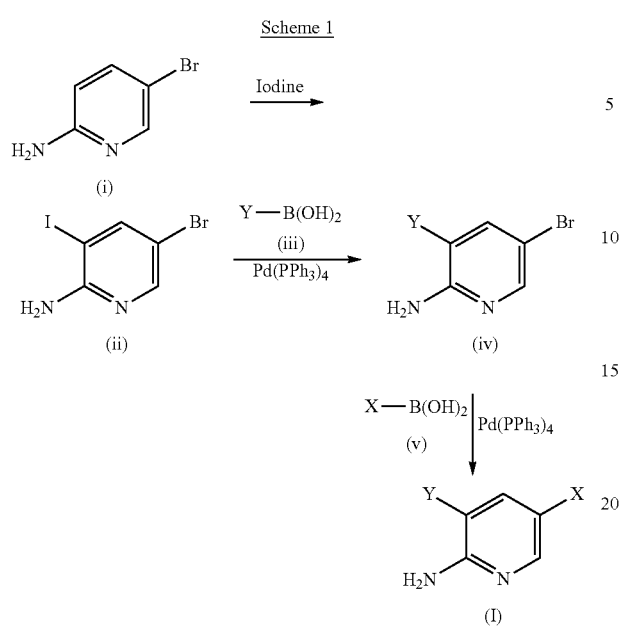

A pyridine according to Formula (i) is treated with iodine in a solvent such as DMSO and heated to give a pyridine according to Formula (ii) which is then reacted with a boronic acid of Formula (iii) under Suzuki reaction conditions (*Miyaura et al.*, 1995, *Chem. Rev.*, 95 (7), pp 2457-2483) to lead to a substituted 5-bromopyridin-2-amine derivative according to Formula (iv) which is then reacted with a boronic acid of Formula (v) under Suzuki reaction conditions to lead to a compound of Formula (I).

Alternatively, compounds of Formula (I) can be obtained as depicted in Scheme 2 below:

Scheme 2

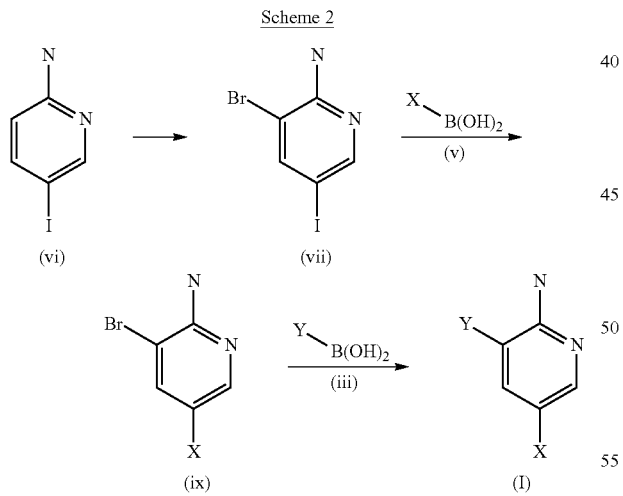

A pyridine of Formula (vi) is treated with a brominating agent (such as N-bromosuccinimide) in a solvent such as acetonitrile to give a pyridine of Formula (vii) (*Zhang et al*, 2004, *J. Med. Chem.* 47, pp 2453-2465) which is then reacted with a boronic acid of Formula (v) under Suzuki reaction conditions (*Miyaura et al.*, 1995, *Chem. Rev.*, 95 (7), pp 2457-2483) to lead to a substituted 3-bromopyridin-2-amine derivative according to Formula (ix) which is then reacted with a boronic acid of Formula (iii) under Suzuki reaction conditions to lead to a compound of Formula (I).

Alternatively, compounds of Formula (I), in particular wherein Y is methoxy pyridine, can s be obtained from intermediate of Formula (iv), in wherein Y is methoxy pyridine, as depicted in Scheme 3 below:

Scheme 3

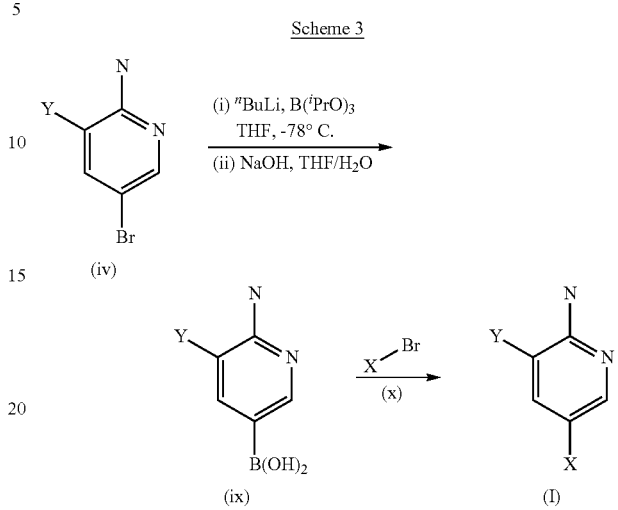

A pyridine of Formula (iv) in a solvent such as tetrahydrofuran is cooled to −78° C. and treated with n-butyl lithium and triisopropyl borate to give a boronic acid of Formula (ix), which is then reacted with a boronic acid of Formula (x) under Suzuki reaction conditions (*Miyaura et al.*, 1995, *Chem. Rev.*, 95 (7), pp 2457-2483) to lead to a compound of Formula (1).

Boronic acids used in the synthesis of compounds according to the invention under Schemes 1 or 2 were commercially available or could be prepared following the general route as described in Schemes 4 and 5 below:

Scheme 4

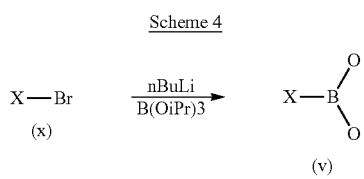

Scheme 5

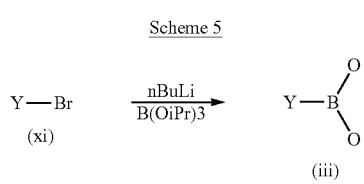

Examples of synthesis of Boronic Acids is also described in *Preparation and Applications in Organic Synthesis and Medicine*, Dennis G. Hall (Editor), ISBN: 978-3-527-30991-7. A bromide of Formula (x) or Formula (xi) in a solvent such as tetrahydrofuran is cooled to −78° C. and treated with n-butyl lithium and triisopropyl borate to give a boronic acid of Formula (v) or Formula (iii) respectively.

If the above synthetic methods are not applicable to obtain aminopyridine derivatives according to the invention and/or necessary intermediates, suitable methods of preparation known by a person skilled in the art should be used. In general, the synthesis pathways for any individual aminopyridine derivative will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, 2005 and Theodora W. Greene and Peter G. M. Wuts in "*Protective Groups in Organic Synthesis*", Wiley Interscience, 4th Edition 2006. Compounds of this invention can be isolated in association with solvent molecules by crystallization from evaporation of an appropriate solvent. The pharmaceutically acceptable acid addition salts of the aminopyridine derivatives, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of an aminopyridine derivative with a suitable base. Both types of salts may be formed or interconverted using ion-exchange resin techniques.

In the following the present invention shall be illustrated by means of some examples, which are not to be viewed as limiting the scope of the invention.

The following abbreviations refer respectively to the definitions below:

equiv. (equivalent), mL (milliliter), g (gram), h (hour), mmol (millimole), ng (nanogram), APCI (atmospheric pressure chemical ionization), RT (room temperature), DCM (dichloromethane), DMSO (Dimethyl Sulfoxide), DAPI (4,6 Diamidino-2-phenylindole), HTS (High Throughput Screening), IR (infrared), LC (Liquid chromatiography), MS (Mass Spectrometry), MHz (Megaherz), NMR (Nuclear magnetic resonance), TLC (Thin layer chromatography), UV (Ultraviolet).

The compounds of invention have been named according to the IUPAC standards used in the program Symyx® Draw (Version 3.2).

The MS, NMR and IR data provided in the examples described below are obtained as followed: Mass spectra: Waters ZQ API MS system + Binary HPLC system with Ultra Violet Diode Array Detector; $H^1$ NMR and $C^{13}$ NMR spectra were recorded on either a Varian Mercury-300 (300 MHz) or Bruker Advance III 400 (400 MHz) with Ultra Shield 400 Plus magnet spectrometer in $CDCl_3$ solution unless otherwise indicated and chemical shifts are reported as δ(ppm) down field from the solvent signal as internal standard for $H^1$ $C^{13}$ NMR. Infrared spectra were recorded on a Perkin-Elmer Paragon 1000FT-IR spectrometer using DCM as solvent. TLC was performed on Merck 60F254 silica plates and visualized by UV light. The compounds were purified by wet flash chromatography using Merck Kieselgel 60 (particle size 70-230 mesh) silica under gravity.

EXAMPLE 1

Synthesis of 3-(6-Methoxypyridin-3-yl)-5-(4-methylsulfonylphenyl) pyridin-2-amine (1)

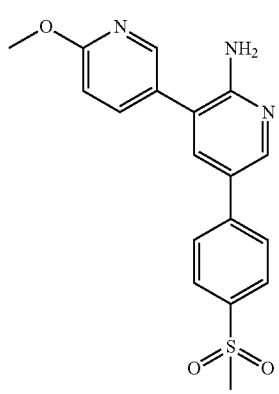

(1)

$K_2CO_3$ aqueous solution (1 M, 5.4 mL) was added to a suspension of 5-bromo-3-(6-methoxypyridin-3-yl)pyridin-2-amine (1.44 g, 5.14 mmol), 4-(methylsulfonyl)phenyl boronic acid (1.08 g, 5.40 mmol, 1.05 equiv.), and $Pd(PPh)_3$ (300 mg, 5 mol %) in dioxane (15 mL) under $N_2$. The reaction mixture was stirred at 120° C. for 14 h, poured onto $H_2O$ (50 mL) and extracted with EtOAc (3×100 mL). The combined organic layers were washed with brine, dried over anhydrous $MgSO_4$ and concentrated in vacuo. The residue was purified by column chromatography on silica gel (hexane/EtOAc, 2/8) providing 3-(6-methoxypyridin-3-yl)-5-(4-methylsulfonylphenyl)pyridin-2-amine (1) (1.92 g, 65%) as a pale yellow solid. IR (thin film/cm$^{-1}$): $v_{max}$ 3378, 1594, 1301, 1148. $H^1$ NMR (400 MHz, $CDCl_3$): δ 8.34 (d, 1H, J=2.0 Hz), 8.26 (d, 1H, J=2.0 Hz), 7.97 (d, 2H, J=8.4 Hz), 7.70 (d, 2H, J=8.4 Hz), 7.69 (d, 1H, J=8.4 Hz), 7.58 (d, 1H, J=2.0 ), 6.86 (d, 1H, J=8.4 Hz), 4.80 (bs, 2H), 3.98 (s, 3H) and 3.06 (s, 3H). $C^{13}$ NMR (100 MHz, $CDCl_3$): δ 164.16, 156.30, 146.94, 146.82, 145.57, 143.34, 139.02, 138.86, 136.92, 128.17, 126.84, 125.84, 118.88, 111.49, 53.67 and 44.62.

The corresponding starting material was prepared as follows:

$I_2$ (8.81 g, 34.7 mmol, 1.2 equiv.) was added to a solution of 5-bromopyridin-2-amine (5.00 g, 28.9 mmol) in DMSO (30 mL), and the resulting mixture was stirred at 100° C. for 4 h. After standing at 25° C. for 12 h, the reaction mixture was poured onto a saturated $Na_2S_2O_5$ aqueous solution (20 mL), and extracted with EtOAc (3×50 mL). The combined organic layers were washed with brine, dried over anhydrous $MgSO_4$ and concentrated in vacuo. The residue was purified by column chromatography on silica gel (hexane/EtOAc, EtOAc 15 to 25%) providing 5-bromo-3-iodopyridin-2-amine (4.00 g, 46%) as a pale yellow solid. $H^1$ NMR (300 MHz, $CDCl_3$): δ 8.07 (s, 1H), 7.98 (s, 1H) and 5.05 (bs, 2H). $K_2CO_3$ aqueous solution (1 M, 6.8 mL) was added to a suspension of 5-bromo-3-iodopyridin-2-amine (2.00 g, 6.69 mmol), 6-methoxypyridin-3-ylboronic acid (1.12 g, 7.32 s mmol, 1.1 equiv.), and $Pd(PPh)_3$ (380 mg, 5 mol %) in dioxane (20 mL) under $N_2$. The reaction mixture was stirred at 120° C. for 14 h, poured onto $H_2O$ (65 mL) and extracted with EtOAc (3×80 mL). The combined organic layers were washed with brine, dried over anhydrous $MgSO_4$ and concentrated in vacuo. The residue was purified by column chromatography on silica gel (hexane/EtOAc, EtOAc 30 to 40%) providing intermediate 5-bromo-3-(6-methoxypyridin-3-yl)pyridin-2-amine (1') (Formula iv) (993 mg, 53%) as a pale yellow solid.

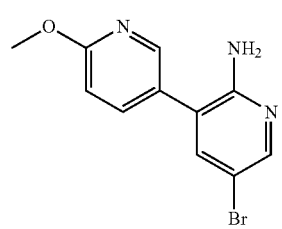

(1')

IR (thin film/cm$^{-1}$): $v_{max}$ 3316, 1605, 1449, 1287. $H^1$ NMR (400 MHz, $CDCl_3$): δ 8.20 (s, 1H), 8.09 (s, 1H), 7.62 (d, 1H, J=8.4 Hz), 7.43 (s, 1H), 6.82 (d, 1H, J=8.4 Hz), 4.20 (bs, 2H) and 3.97 (s, 3H). $C^{13}$ NMR (100 MHz, $CDCl_3$): δ 164.18, 154.84, 147.34, 146.73, 140.29, 138.74, 125.22, 120.40, 111.47, 108.49 and 53.67.

EXAMPLE 2

Synthesis of Further Compounds of the Invention

The following compounds listed in Table 1 below were prepared using an analogous procedure to procedure described in Example 1 and the corresponding intermediates (2')-(9') of Formula (iv), respectively.

TABLE 1

| Compound | Chemical name | Structure | MS m/z [M + H]+ |
|---|---|---|---|
| 2 | 5-(4-methylsulfonylphenyl)-3-[3-(trifluoromethyl)phenyl]pyridin-2-amine | 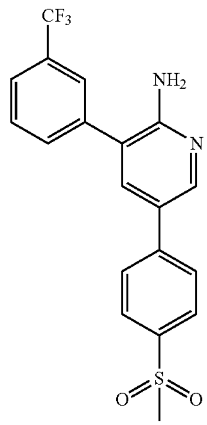 [SMILES: CS(=O)(=O)c1ccc(-c2cnc(N)c(-c3cccc(C(F)(F)F)c3)c2)cc1] | 393 |
| 3 | 3-[2-amino-5-(4-methylsulfonylphenyl) pyridin-3-yl]phenol | 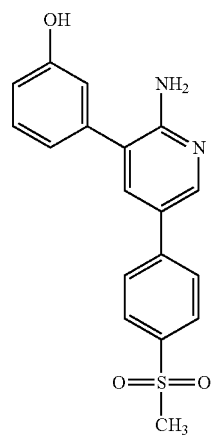 [SMILES: CS(=O)(=O)c1ccc(-c2cnc(N)c(-c3cccc(O)c3)c2)cc1] | 341 |
| 4 | 4-[2-amino-5-(4-methylsulfonylphenyl) pyridin-3-yl]-2-methoxyphenol | 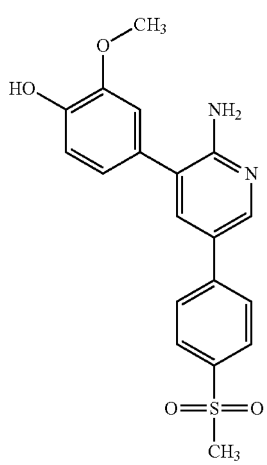 [SMILES: COc1cc(-c2cc(-c3ccc(S(C)(=O)=O)cc3)cnc2N)ccc1O] | 371 |

TABLE 1-continued

| Compound | Chemical name | Structure | MS m/z [M + H]+ |
|---|---|---|---|
| 5 | 4-[2-amino-5-(4-methylsulfonylphenyl) pyridin-3-yl]phenol | 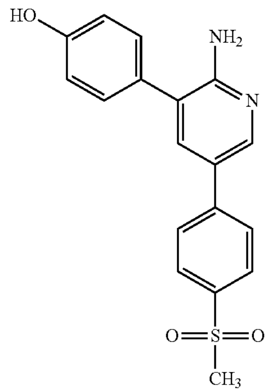 [SMILES: CS(=O)(=O)c1ccc(-c2cnc(N)c(-c3ccc(O)cc3)c2)cc1] | 341 |
| 6 | 4-[2-amino-5-(6-methoxypyridin-3-yl) pyridin-3-yl]-2-methoxyphenol | 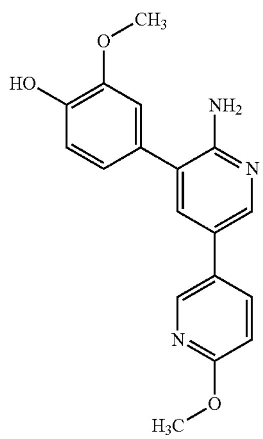 [SMILES: COc1ccc(-c2cnc(N)c(-c3ccc(O)c(OC)c3)c2)cn1] | 324 |
| 7 | 4-[6-amino-5-[4-(4-methylpiperazin-1-yl) phenyl]pyridin-3-yl]-2,6-dimethylphenol | 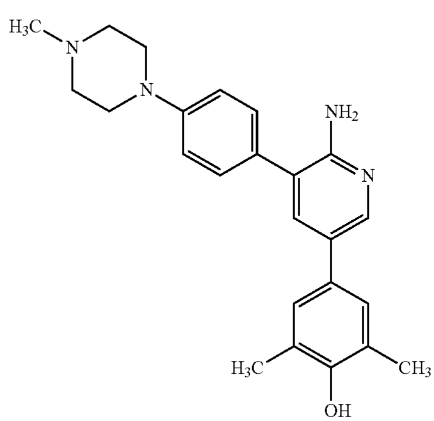 | 389 |

TABLE 1-continued

| Compound | Chemical name | Structure | MS m/z [M + H]+ |
|---|---|---|---|
| 8 | [4-[6-amino-5-(6-methoxypyridin-3-yl) pyridin-3-yl]phenyl]methanol | 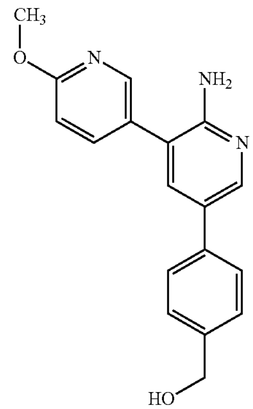 [SMILES: COc1ccc(-c2cc(-c3ccc(CO)cc3)cnc2N)cn1] | 308 |
| 9 | 4-[6-amino-5-[4-(4-methylpiperazin-1-yl) phenyl]pyridin-3-yl]phenol | 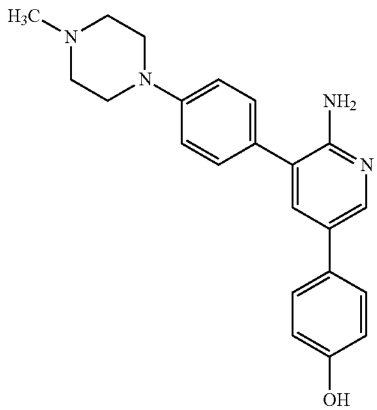 [SMILES: CN1CCN(c2ccc(-c3cc(-c4ccc(O)cc4)cnc3N)cc2)CC1] | 361 |

Characterizing data for compound 2: $^1$H NMR (400 MHz, CDCl$_3$): δ 8.41 (d, 1H, J=2.4 Hz), 8.01-7.98 (m, 2H), 7.77-7.63 (m, 7H), 4.73 (bs, 2H) and 3.08 (s, 3H).

Intermediates of Formula (iv) wherein Y are as defined in the detailed description were used:

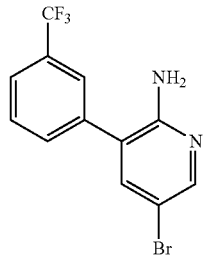

5-bromo-3-[3-(trifluoromethyl)phenyl]pyridin-2-amine (2');

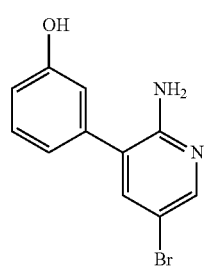

3-(2-amino-5-bromo-3-pyridyl)phenol (3');

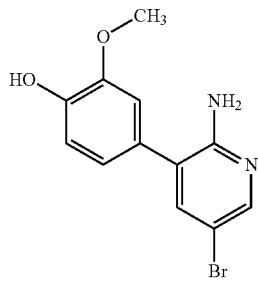

4-(2-amino-5-bromo-3-pyridyl)-2-methoxy-phenol (4');

-continued

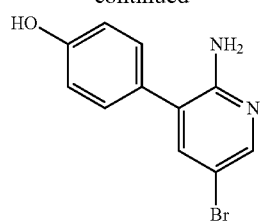

4-(2-amino-5-bromo-3-pyridyl)phenol (5');

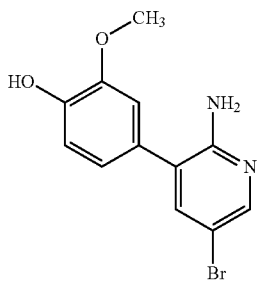

4-(2-amino-5-bromo-3-pyridyl)-2-methoxy-phenol (6');

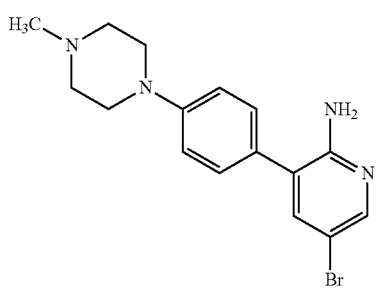

5-bromo-3-[4-(4-methylpiperazin-1-yl)phenyl]pyridin-2-amine (7');

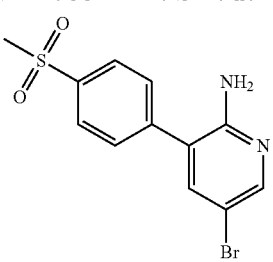

5-bromo-3-(4-methylsulfonyl)phenyl)pyridin-2-amine (8');

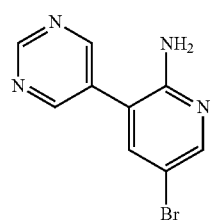

5-bromo-3-(pyrimidin-5-yl)pyridin-2-amine (9');

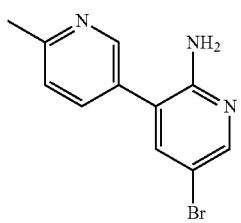

5-bromo-6'-methyl-3,3'-bipyridin-2-amine (10');

-continued

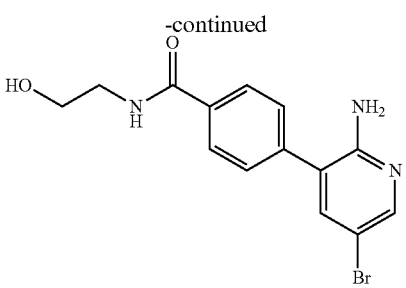

4-(2-amino-5-bromopyridin-3-yl)-N-(2-hydroxyethyl)benzamide (11');

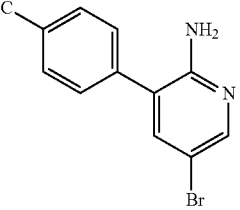

5-bromo-3-(4-trifluoromethyl)phenyl)pyridin-2-amine (12'); and

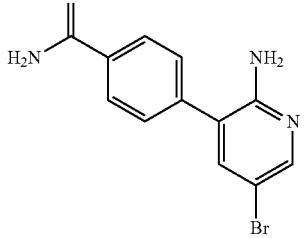

4-(2-amino-5-bromopyridin-3-yl)benzamide (13').

Intermediate of Formula (viii) wherein X are as defined in the detailed description was used:

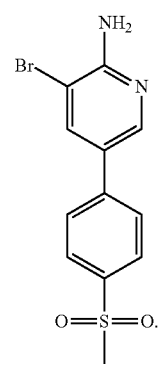

3-bromo-5-(4-(methylsulfonyl)phenyl)pyridin-2-amine (14')

Intermediate of Formula (iii) or (v) wherein X and Y are as defined in the detailed description was used:

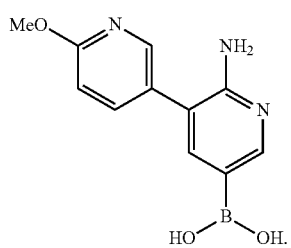

2-amino-6'-methoxy-3,3'-bipyridin-5-ylboronic acid (15')

The following compounds listed in Table 2 below were prepared using an analogous procedure to the procedure described in Example 1:

TABLE 2

| N° | Chemical name | Structure | MS m/z [M + H]⁺ | ¹H NMR |
|---|---|---|---|---|
| 10 | (N,N-dimethyl) {4-[2-amino-3-(2-methoxypyridin-5-yl)pyridin-5-yl] benzene} sulfonamide | 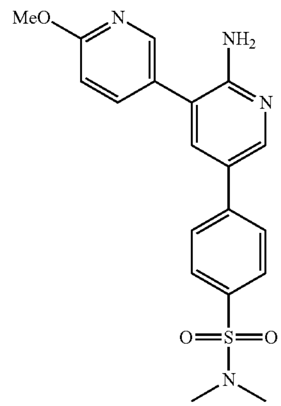 [SMILES: COc1ccc(-c2cc(-c3ccc(S(=O)(=O)N(C)C)cc3)cnc2N)cn1] | 385 | 300 MHz, CDCl3; δ 8.32 (d, 1H, J = 2.4 Hz), 8.28 (dd, 1H, J = 2.4 & 0.9 Hz), 7.84 (d, 2H, J = 8.7 Hz), 7.69 (m, 4H), 6.89 (dd, 1H, J = 8.7 & 0.9 Hz), 5.22 (bs, 2H), 4.00 (s, 3H) & 2.74 (s, 6H) |
| 11 | 4-[2-amino-3-(2-methoxypyridin-5-yl)pyridin-5-yl]-N,N-dimethyl benzamide | 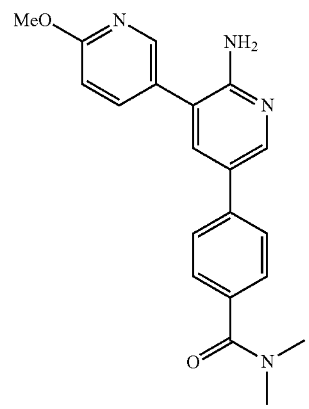 [SMILES: COc1ccc(-c2cc(-c3ccc(C(=O)N(C)C)cc3)cnc2N)cn1] | 349 | 300 MHz, CDCl3; δ 8.31 (d, 1H, J = 2.4 Hz), 8.27 (d, 1H, J = 2.4 Hz), 7.70 (dd, 1H, J = 8.4 & 2.4 Hz), 7.59 (d, 1H, J = 2.4 Hz), 7.55 (d, 2H, J = 8.4 Hz), 7.48 (d, 2H, J = 8.4 Hz), 6.86 (d, 1H, J = 8.4 Hz), 4.88 (bs, 2H), 3.98 (s, 3H) & 3.09 (bs, 3H), 3.04 (bs, 3H) |
| 12 | 5-(2-methoxy pyridin-5-yl)-3-[4-(methylsulfonyl) phenyl] pyridin-2-amine | 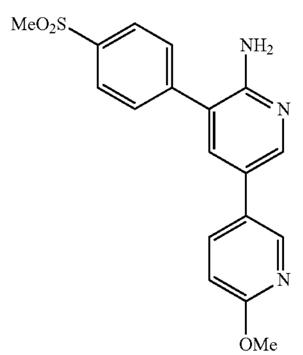 [SMILES: COc1ccc(-c2cnc(N)c(-c3ccc(S(C)(=O)=O)cc3)c2)cn1] | 356 | 300 MHz, CDCl3; δ 8.31 (d, 1H, J = 2.4 Hz), 8.27 (d, 1H, J = 2.4 Hz), 7.70 (dd, 1H, J = 8.4 & 2.4 Hz), 7.59 (d, 1H, J = 2.4 Hz), 7.55 (d, 2H, J = 8.4 Hz), 7.48 (d, 2H, J = 8.4 Hz), 6.86 (d, 1H, J = 8.4 Hz), 4.88 (bs, 2H), 3.98 (s, 3H) & 3.09 (bs, 3H), 3.04 (bs, 3H) |
| 13 | 5-[4-(methyl sulfonyl)phenyl]-3-(pyrimidin-5-yl)pyridin-2-amine | 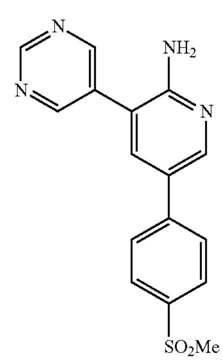 [SMILES: CS(=O)(=O)c1ccc(-c2cnc(N)c(-c3cncnc3)c2)cc1] | 327 | 400 MHz, DMSO-d6; δ 9.16 (s, 1H), 8.91 (s, 2H), 8.46 (d, 1H, J = 2.4 Hz), 7.92 (d, 2H, J = 8.8 Hz), 7.89 (d, 2H, J = 8.8 Hz), 7.84 (d, 1H, 2.4 Hz), 6.27 (s, 2H), 3.19 (s, 3H) |

TABLE 2-continued

| N° | Chemical name | Structure | MS m/z [M + H]+ | 1H NMR |
|---|---|---|---|---|
| 14 | (Morpholino) {4-[2-amino-3-(2-methoxypyridin-5-yl)pyridin-5-yl] benzene} sulfonamide | 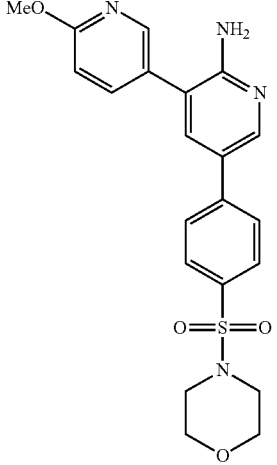 [SMILES: COc1ccc(-c2cc(-c3ccc(S(=O)(=O)N4CCOCC4)cc3)cnc2N)cn1] | 427 | 300 MHz, CDCl$_3$; δ 8.33 (d, 1H, J = 2.4 Hz), 8.27 (d, 1H, J = 2.4 Hz), 7.79 (d, 2H, J = 8.4 Hz), 7.70 (d, 1H, J = 2.4 Hz), 7.67 (d, 2H, J = 8.4 Hz), 7.60 (d, 1H, J = 2.4 Hz), 6.87 (d, 1H, J = 8.4 Hz), 4.94 (bs, 2H), 3.98 (s, 3H), 3.74 (bt, 4H, J = 4.8 Hz) & 3.03 (bt, 4H, J = 4.8 Hz) |
| 15 | 3,5-di(2-methoxy pyridin-5-yl) pyridin-2-amine | 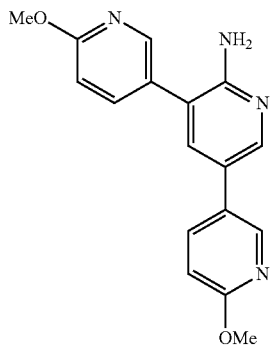 [SMILES: COc1ccc(-c2cnc(N)c(-c3ccc(OC)nc3)c2)cn1] | 309 | 300 MHz, DMSO-d$_6$: δ 8.43 (dd, 1H, J = 2.4 & 0.6 Hz), 8.29 (dd, 1H, J = 2.4 & 0.9 Hz), 8.27 (d, 1H, J = 2.4 Hz), 7.97 (dd, 1H, J = 8.7 & 2.7 Hz), 7.84 (dd, 1H, J = 8.7 & 2.7 Hz), 7.61 (d, 1H, J = 2.7 Hz), 6.88 (m, 2H, J = 7.8 Hz), 5.71 (bs, 2H), 3.91 (s, 3H) & 3.88 (s, 3H) |
| 16 | (N-methyl piperazin) {4-[2-amino-3-(2-methoxypyridin-5-yl)pyridin-5-yl] benzene} sulfonamide | 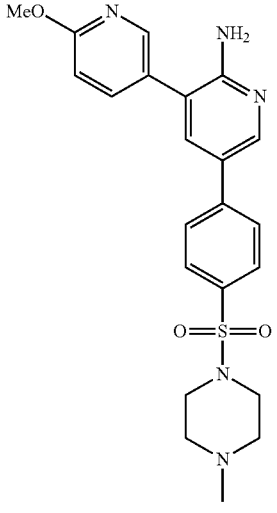 [SMILES: COc1ccc(-c2cc(-c3ccc(S(=O)(=O)N4CCN(C)CC4)cc3)cnc2N)cn1] | 440 | 300 MHz, CDCl$_3$: δ 8.35 (d, 1H, J = 2.4 Hz), 8.29 (d, 1H, J = 2.4 Hz), 7.79 (dt, 1H, J = 8.7 & 1.8 Hz), 7.72 (dd, 1H, J = 8.4 & 2.4 Hz), 7.67 (dt, 2H, J = 8.7 & 1.8 Hz), 7.56 (d, 1H, J = 2.4 Hz), 6.88 (d, 1H, J = 8.4 Hz), 4.71 (bs, 2H), 4.00 (s, 3H), 3.10 (bt, 4H, J = 5.1 Hz), 2.53 (bt, 4H, J = 5.1 Hz) & 2.29 (s, 3H) |

TABLE 2-continued

| N° | Chemical name | Structure | MS m/z [M + H]+ | 1H NMR |
|---|---|---|---|---|
| 17 | 3,5-di-[4-(methyl sulfonyl) phenyl]pyridin-2-amine | 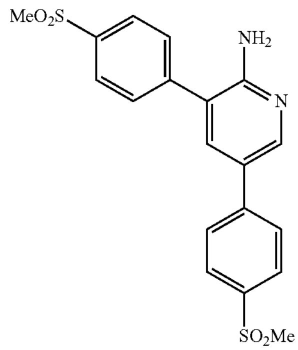 [SMILES: CS(=O)(=O)c1ccc(-c2cnc(N)c(-c3ccc(S(C)(=O)=O)cc3)c2)cc1] | 403 | 400 MHz, DMSO-d6: δ 8.48 (d, 1H, J = 2.4 Hz), 8.03 (d, 2H, J = 8.4 Hz), 7.97 (d, 2H, J = 9.2 Hz), 7.94 (d, 2H, J = 9.2 Hz), 7.84 (d, 2H, J = 8.4 Hz), 7.81 (d, 1H, J = 2.4 Hz), 6.17 (bs, 2H), 3.27 (s, 3H) & 3.23 (s, 3H) |
| 18 | 3-(2-methoxy pyridin-5-yl)-5-[3-(methyl sulfonyl)phenyl] pyridin-2-amine | 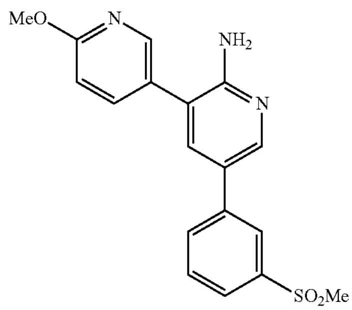 [SMILES: COc1ccc(-c2cc(-c3cccc(S(C)(=O)=O)c3)cnc2N)cn1] | 356 | 400 MHz, DMSO-d6: δ 8.41 (d, 1H, J = 2.4 Hz), 8.31 (d, 1H, J = 2.4 Hz), 8.15 (bt, 1H, J = 1.6 Hz), 8.03 (m, 1H), 7.86 (dd, 1H, J = 8.4 & 2.4 Hz), 7.82 (m, 1H), 7.77 (d, 1H, J = 2.4 Hz), 7.68 (t, 1H, J = 8.0 Hz), 6.93 (d, 1H, J = 8.4 Hz), 5.97 (bs, 2H), 3.92 (s, 3H) & 3.28 (s, 3H) |
| 21 | (N-methyl) {4-[2-amino-3-(2-methoxypyridin-5-yl)pyridin-5-yl] benzene} sulfonamide | 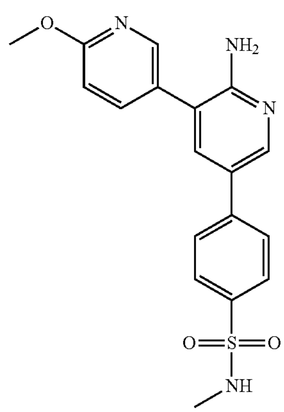 [SMILES: CNS(=O)(=O)c1ccc(-c2cnc(N)c(-c3ccc(OC)nc3)c2)cc1] | 371 | 400 MHz, CDCl3: δ 8.26 (d, 1H, J = 2.0 Hz), 8.32 (d, 1H, J = 2.4 Hz), 7.88 (d, 2H, J = 8.4 Hz), 7.69 (dd, 1H, J = 8.4 & 2.4 Hz), 7.64 (d, 2H, J = 8.4 Hz), 7.56 (d, 1H, J = 2.0 Hz), 6.85 (d, 1H, J = 8.8 Hz), 4.81 (bq, 1H, J = 5.2 Hz), 4.76 (bs, 2H), 3.97 (s, 3H) & 2.68 (d, 3H, J = 5.2 Hz) |
| 22 | 4-[2-amino-3-(2-methoxypyridin-5-yl)pyridin-5-yl]-N-methyl benzamide | 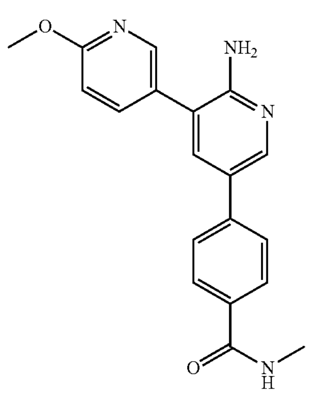 | 335 | 400 MHz, DMSO-d6: δ 8.41 (m, 1H), 8.39 (d, 1H, J = 2.4 Hz), 8.31 (d, 1H, J = 2.4 Hz), 7.88 (d, 2H, J = 8.4 Hz), 7.86 (dd, 1H, J = 8.4 & 2.4 Hz), 7.75 (d, 2H, J = 8.4 Hz), 7.70 (d, 1H, J = 2.4 Hz), 6.92 (d, 1H, J = 8.4 Hz), 5.91 (bs, 2H), 3.92 (s, 3H) & 2.80 (d, 3H, J = 4.4 Hz) |

TABLE 2-continued

| N° | Chemical name | Structure | MS m/z [M + H]+ | 1H NMR |
|---|---|---|---|---|
| 23 | {4-[2-amino-3-(2-methoxy pyridin-5-yl) pyridin-5-yl] phenyl}-(morpholino)-methanone | 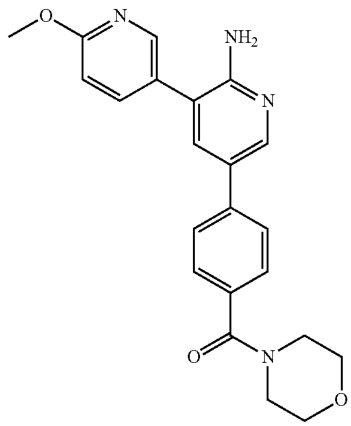 [SMILES: COc1ccc(-c2cc(-c3ccc(C(=O)N4CCOCC4)cc3)cnc2N)cn1] | 391 | 400 MHz, DMSO-d6: δ 8.35 (d, 1H, J = 2.4 Hz), 8.31 (dd, 1H, J = 2.4 & 0.8 Hz), 7.86 (dd, 1H, J = 8.4 & 2.4 Hz), 7.73 (d, 2H, J = 8.4 Hz), 7.67 (d, 1H, J = 2.4 Hz), 7.45 (d, 2H, J = 8.4 Hz), 6.92 (d, 1H, J = 8.4 Hz), 5.89 (bs, 1H), 3.92 (s, 3H) & 3.68-3.42 (m, 8H) |
| 24 | 4-[2-amino-3-(2-methoxypyridin-5-yl)pyridin-5-yl] benzamide | 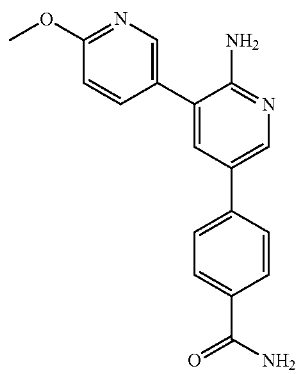 [SMILES: COc1ccc(-c2cc(-c3ccc(C(N)=O)cc3)cnc2N)cn1] | 321 | 400 MHz, DMSO-d6: δ 8.39 (s, 1H), 8.31 (s, 1H), 8.00 (s, 1H), 7.92 (d, 2H, J = 8.0 Hz), 7.86 (d, 1H, J = 8.4 Hz), 7.75 (d, 2H, J = 8.0 Hz), 7.71 (s, 1H), 7.34 (bs, 1H), 6.93 (d, 1H, J = 8.4 Hz), 5.97 (bs, 2H) & 3.91 (s, 3H) |
| 27 | 4-[6-amino-5-(2-methoxypyridin-5-yl)pyridin-3-yl] benzoic acid | 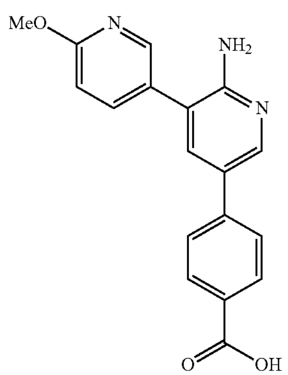 [SMILES: COc1ccc(-c2cc(-c3ccc(C(=O)O)cc3)cnc2N)cn1] | 322 | 400 MHz, DMSO-d6: δ 8.39 (d, 1H, J = 2.4 Hz), 8.30 (d, 1H, J = 2.4 Hz), 7.95 (d, 2H, J = 8.4 Hz), 7.86 (dd, 1H, J = 8.4 & 2.4 Hz), 7.77 (d, 2H, J = 8.4 Hz), 7.70 (d, 1H, J = 2.4 Hz), 6.93 (d, 1H, J = 8.4 Hz), 6.00 (bs, 2H) & 3.91 (s, 3H) |
| 48 | N-{4-[2-amino-3-(2-methoxy pyridin-5-yl) pyridin-5-yl] benzene}methyl sulfonamide | 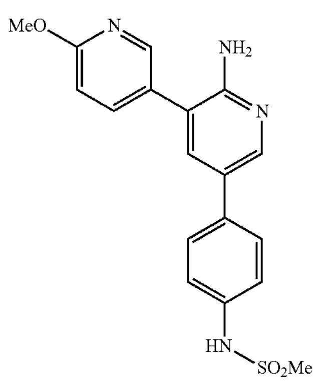 [SMILES: COc1ccc(-c2cc(-c3ccc(NS(C)(=O)=O)cc3)cnc2N)cn1] | 371 | 400 MHz, DMSO-d6: δ 9.74 (s, 1H), 8.28-8.26 (m, 2H), 7.84 (dd, 1H, J = 8.4 & 2.4 Hz), 7.62 (d, 2H, J = 8.4 Hz), 7.59 (d, 1H, J = 2.4 Hz), 7.24 (d, 2H, J = 8.4 Hz), 6.91 (d, 1H, J = 8.4 Hz), 5.82 (bs, 2H), 3.90 (s, 3H) & 2.99 (s, 3H) |

TABLE 2-continued

| N° | Chemical name | Structure | MS m/z [M + H]+ | 1H NMR |
|---|---|---|---|---|
| 49 | 4-[6-amino-5-(6-methoxypyridin-3-yl)pyridin-3-yl]-N-(3-hydroxypropyl)-benzamide | 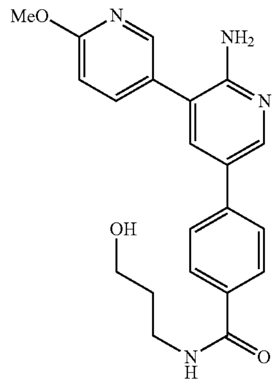 [SMILES: COc1ccc(-c2cc(-c3ccc(C(=O)NCCCO)cc3)cnc2N)cn1] | 379 | 400 MHz, DMSO-$d_6$: δ 8.45 (s, 1H), 8.38 (s, 1H), 8.30 (s, 1H), 7.88-7.84 (m, 3H), 7.75 (d, 2H, J = 8.0 Hz), 7.69 (s, 1H), 6.92 (d, 1H, J = 8.4 Hz), 5.96 (bs, 2H), 4.48 (t, 1H, J = 5.2 Hz), 3.90 (s, 3H), 3.46 (q, 2H, J = 5.2 Hz), 3.31 (s, 2H) & 1.68 (t, 2H, J = 6.4 Hz) |
| 50 | 5-(benzo[c][1,2,5]-oxadiazol-6-yl)-3-(2-methoxypyridin-5-yl)pyridin-2-amine | 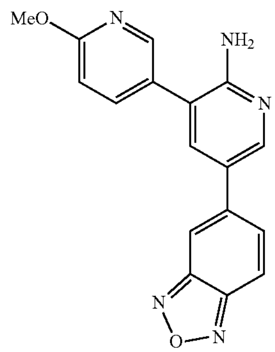 [SMILES: COc1ccc(-c2cc(-c3ccc4nonc4c3)cnc2N)cn1] | 320 | 400 MHz, DMSO-$d_6$: δ 8.55 (d, 1H, J = 2.4 Hz), 8.33 (d, 1H, J = 2.4 Hz), 8.27 (d, 1H, J = 0.8 Hz), 8.08 (s, 2H), 7.88-7.85 (m, 2H), 6.93 (d, 1H, J = 8.4 Hz), 6.22 (s, 2H) & 3.91 (s, 3H) |
| 51 | N-cyclopropyl-{4-[2-amino-3-(2-methoxypyridin-5-yl)pyridin-5-yl]benzene}sulfonamide | 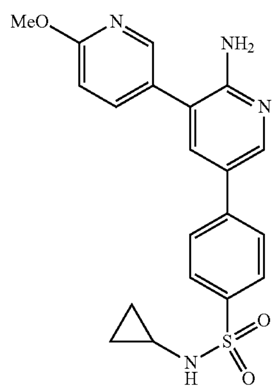 [SMILES: COc1ccc(-c2cc(-c3ccc(S(=O)(=O)NC4CC4)cc3)cnc2N)cn1] | 397 | 400 MHz, DMSO-$d_6$: δ 8.41 (d, 1H, J = 2.4 Hz), 8.30 (d, 1H, J = 2.4 Hz), 7.01-7.89 (m, 3H), 7.85 (dd, 1H, J = 8.4 & 2.4 Hz), 7.80 (d, 2H, J = 8.4 Hz), 7.73 (d, 1H, J = 2.4 Hz), 6.92 (d, 1H, J = 8.4 Hz), 6.05 (bs, 2H), 3.90 (s, 3H), 2.11-2.08 (m, 1H), 0.47 (q, 2H, J = 4.4 Hz) & 0.40 (q, 2H, J = 4.4 Hz) |
| 52 | 5-(H-imidazo[1,2-a]pyridin-6-yl)-3-(2-methoxypyridin-5-yl)pyridin-2-amine | 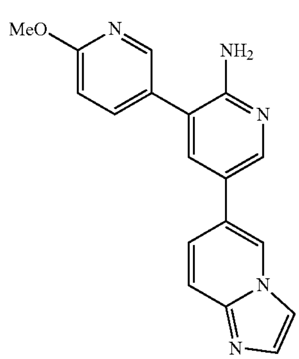 [SMILES: COc1ccc(-c2cc(-c3ccc4nccn4c3)cnc2N)cn1] | 318 | 400 MHz, DMSO-$d_6$: δ 8.89 (s, 1H), 8.32 (dd, 2H, J = 9.6 & 2.0 Hz), 7.84-7.88 (m, 2H), 7.68 (d, 1H, J = 2.0 Hz), 7.59-7.56 (m, 3H), 6.93 (d, 1H, J = 8.4 Hz), 5.92 (bs, 2H) & 3.90 (s, 3H) |

TABLE 2-continued

| N° | Chemical name | Structure | MS m/z [M + H]+ | 1H NMR |
|---|---|---|---|---|
| 53 | 3-(2-methoxy pyridin-5-yl)-5-(1-methyl-1H-indazol-6-yl)pyridin-2-amine | 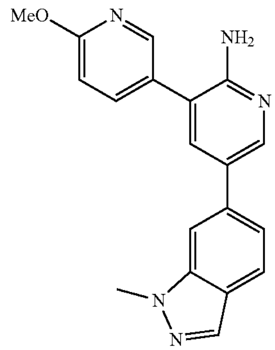 [SMILES: COc1ccc(-c2cc(-c3ccc4cnn(C)c4c3)cnc2N)cn1] | 332 | 400 MHz, DMSO-d6: δ 8.44 (d, 1H, J = 2.4 Hz), 8.33 (d, 1H, J = 2.4 Hz), 8.02 (s, 1H), 7.91 (s, 1H), 7.88 (dd, 1H, J = 8.4 & 2.4 Hz), 7.78-7.76 (m, 2H), 7.46 (d, 1H, J = 8.4 Hz), 6.94 (d, 1H, J = 8.4 Hz), 5.60 (bs, 2H), 4.08 (s, 3H) & 3.92 (s, 3H) |
| 54 | 4-[2-amino-3-(2-methoxypyridin-5-yl)pyridin-5-yl]-N-cyclopropyl benzamide | 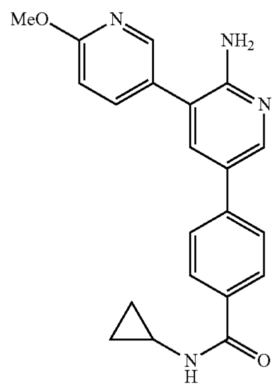 [SMILES: COc1ccc(-c2cc(-c3ccc(C(=O)NC4CC4)cc3)cnc2N)cn1] | 361 | 400 MHz, DMSO-d6: δ 8.44 (d, 1H, J = 3.2 Hz), 8.39 (d, 1H, J = 2.4 Hz), 8.30 (d, 1H, J = 2.4 Hz), 7.78-7.76 (m, 3H), 7.75 (d, 2H, J = 8.4 Hz), 7.70 (d, 1H, J = 2.4 Hz), 6.92 (d, 1H, J = 12.4 Hz), 5.97 (bs, 2H), 3.91 (s, 3H), 2.88-2.84 (m, 1H), 0.70-0.69 (m, 2H) & 0.59-0.58 (m, 2H) |
| 60 | 4-[2-amino-3-(2-methoxypyridin-5-yl)pyridin-5-yl]-N-(2-morpholino ethyl)benzamide | 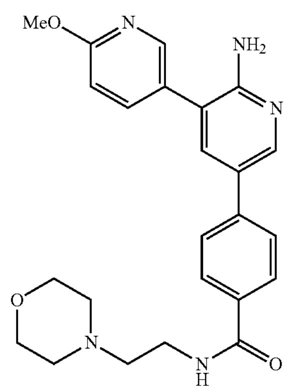 [SMILES: COc1ccc(-c2cc(-c3ccc(C(=O)NCCN4CCOCC4)cc3)cnc2N)cn1] | 434 | 400 MHz, DMSO-d6: δ 8.44-8.39 (m, 2H), 8.30 (d, 1H, J = 1.6 Hz), 7.89-7.84 (m, 3H), 7.76 (d, 2H, J = 8.4 Hz), 7.71 (d, 1H, J = 2.0 Hz), 6.93 (d, 1H, J = 8.4 Hz), 5.97 (bs, 2H), 3.91 (s, 3H), 3.57 (s, 4H), 3.40-3.38 (m, 2H) & 2.49-2.42 (m, 6H) |
| 61 | 3-[2-amino-3-(2-methoxypyridin-5-yl)pyridin-5-yl]benzamide | 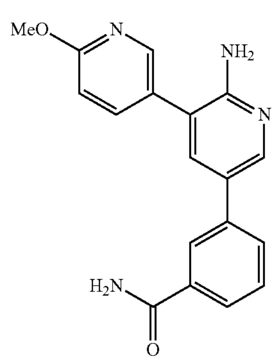 [SMILES: COc1ccc(-c2cc(-c3cccc(C(N)=O)c3)cnc2N)cn1] | 321 | 400 MHz, DMSO-d6: δ 8.38 (s, 1H), 8.31 (s, 1H), 8.12 (s, 1H), 8.07 (s, 1H), 7.87-7.77 (m, 3H), 7.73 (s, 1H), 7.49 (t, 1H, J = 7.6 Hz), 7.42 (s, 1H), 6.93 (d, 1H, J = 8.4 Hz), 5.92 (bs, 2H) & 3.91 (s, 3H) |

TABLE 2-continued

| N° | Chemical name | Structure | MS m/z [M + H]+ | 1H NMR |
|---|---|---|---|---|
| 62 | 3-(2-methoxypyridin-5-yl)-5-[4-(5-methyl-1,3,4-oxadiazol-2-yl)phenyl]pyridin-2-amine | 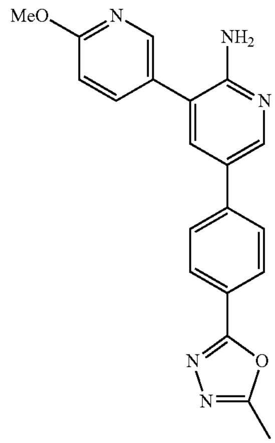 [SMILES: COc1ccc(-c2cc(-c3ccc(-c4nnc(C)o4)cc3)cnc2N)cn1] | 360 | 400 MHz, DMSO-$d_6$: δ 8.43 (s, 1H), 8.31 (s, 1H), 7.98 (d, 2H, J = 8.0 Hz), 7.88-7.85 (m, 3H), 7.74 (s, 1H), 6.93 (s, 1H), 6.04 (bs, 2H), 3.91 (s, 3H) & 2.59 (s, 3H) |
| 63 | 3-(2-methoxypyridin-5-yl)-5-(6-morpholino-pyridin-3-yl)pyridin-2-amine | 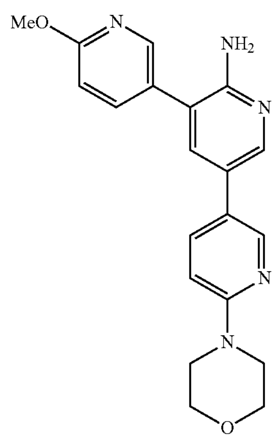 [SMILES: COc1ccc(-c2cc(-c3ccc(N4CCOCC4)nc3)cnc2N)cn1] | 364 | 400 MHz, DMSO-$d_6$: δ 8.43 (s, 1H), 8.29 (s, 1H), 8.25 (s, 1H), 7.87-7.83 (m, 2H), 7.60 (s, 1H), 6.93-6.88 (m, 2H), 5.81 (bs, 2H), 3.91 (s, 3H), 3.71 (t, 4H, J = 4.4 Hz) & 3.46 (t, 4H, J = 4.4 Hz) |
| 64 | 5-[4-(1H-pyrazol-1-yl)phenyl]-3-(2-methoxypyridin-5-yl)pyridin-2-amine | 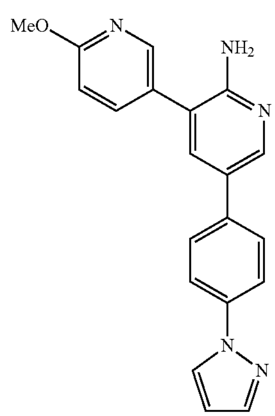 [SMILES: COc1ccc(-c2cc(-c3ccc(-n4cccn4)cc3)cnc2N)cn1] | 344 | 400 MHz, DMSO-$d_6$: δ 8.54 (d, 1H, J = 2.4 Hz), 8.36 (d, 1H, J = 2.4 Hz), 8.31 (d, 1H, J = 2.4 Hz), 7.88-7.84 (m, 3H), 7.79-7.74 (m, 3H), 7.68 (d, 1H, J = 2.4 Hz), 6.92 (d, 1H, J = 8.4 Hz), 6.55 (t, 1H, J = 2.0 Hz), 5.88 (bs, 2H) & 3.90 (s, 3H) |

TABLE 2-continued

| N° | Chemical name | Structure | MS m/z [M + H]+ | 1H NMR |
|---|---|---|---|---|
| 66 | 3-(2-methoxy pyridin-5-yl)-5-(quinolin-6-yl) pyridin-2-amine | 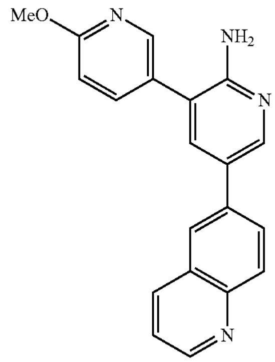 [SMILES: COc1ccc(-c2cc(-c3ccc4ncccc4c3)cnc2N)cn1] | 329 | 400 MHz, DMSO-d$_6$: δ 8.86-8.85 (m, 1H), 8.51 (d, 1H, J = 2.0 Hz), 8.37-8.33 (m, 2H), 8.28 (s, 1H), 8.13 (d, 1H, J = 8.8 Hz), 8.04 (d, 1H, J = 8.8 Hz), 7.89 (dd, 1H, J = 8.4 and 2.4 Hz), 7.84 (d, 1H, J = 2.0 Hz), 7.54 (dd, 1H, J = 8.4 and 4.0 Hz), 6.95 (d, 1H, J = 8.4 Hz), 5.99 (bs, 2H) & 3.92 (s, 3H) |
| 67 | 4-[2-amino-3-(2-methoxypyridin-5-yl)pyridin-5-yl]-N-[2-(pyrrolidin-1-yl) ethyl] benzamide | 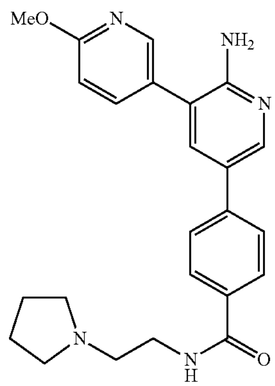 [SMILES: COc1ccc(-c2cc(-c3ccc(C(=O)NCCN4CCCC4)cc3)cnc2N)cn1] | 418 | 400 MHz, DMSO-d$_6$: δ 8.45 (s, 1H), 8.39 (s, 1H), 8.31 (s, 1H), 7.90-7.85 (m, 3H), 7.77-7.75 (m, 2H), 7.71 (s, 1H), 6.93 (d, 1H, J = 8.4 Hz), 5.97 (bs, 2H), 3.91 (s, 3H), 3.39 (d, 2H, J = 6.0 Hz), 3.34 (s, 1H), 2.58 (t, 2H, J = 6.8 Hz), 2.51 (s, 4H) & 1.68 (s, 4H) |
| 68 | 5-[2-(trifluoro methyl)-4-(methylsulfonyl) phenyl]-3-(2-methoxypyridin-5-yl)pyridin-2-amine | 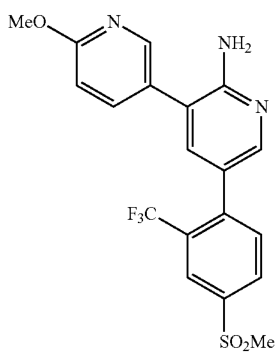 [SMILES: COc1ccc(-c2cc(-c3ccc(S(C)(=O)=O)cc3C(F)(F)F)cnc2N)cn1] | 424 | 400 MHz, DMSO-d$_6$: δ 8.28 (d, 1H, J = 1.6 Hz), 8.25 (s, 1H), 8.23 (d, 1H, J = 2.0 Hz), 7.96 (d, 1H, J = 8.8 Hz), 7.81-7.79 (m, 2H), 7.37 (d, 1H, J = 2.0 Hz), 6.91 (d, 1H, J = 8.4 Hz), 6.10 (bs, 2H), 3.89 (s, 3H) & 3.37 (s, 3H) |
| 71 | {4-[2-amino-3-(4-carbamoyl phenyl)pyridin-5-yl]phenyl}-(morpholino) methanone | 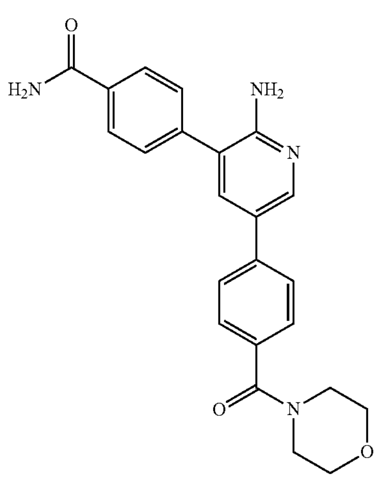 [SMILES: NC(=O)c1ccc(-c2cc(-c3ccc(C(=O)N4CCOCC4)cc3)cnc2N)cc1] | 403 | 400 MHz, DMSO-d$_6$: δ 8.37 (d, 1H, J = 2.8 Hz), 8.00 (d, 3H, J = 8.4 Hz), 7.73 (d, 2H, J = 8.4 Hz), 7.70 (d, 1H, J = 2.4 Hz), 7.63 (d, 2H, J = 8.4 Hz), 7.45 (d, 2H, J = 8.4 Hz), 7.36 (bs, 1H), 5.89 (bs, 2H), 3.61 (bs, 4H) & 3.51 (bs, 4H) |

TABLE 2-continued

| N° | Chemical name | Structure | MS m/z [M + H]+ | 1H NMR |
|---|---|---|---|---|
| 73 | 4-[2-amino-3-(2-methylpyridin-5-yl)pyridin-5-yl] benzamide | 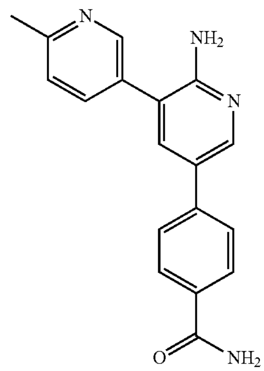 [SMILES: Cc1ccc(-c2cc(-c3ccc(C(N)=O)cc3)cnc2N)cn1] | 305 | 400 MHz, DMSO-$d_6$: δ 8.74 (d, 1H, J = 2.0 Hz), 8.34 (d, 1H, J = 2.4 Hz), 8.04 (s, 1H), 7.99 (d, 2H, J = 8.4 Hz), 7.95 (dd, 1H, J = 8.0 & 2.4 Hz), 7.69 (d, 1H, J = 2.4 Hz), 7.62 (d, 2H, J = 8.4 Hz), 7.40 (s, 1H), 7.28 (d, 1H, J = 8.0 Hz), 5.90 (bs, 2H) & 2.48 (s, 3H) |
| 74 | 4-[2-amino-5-[4-(4-morpholinylcarbonyl)phenyl]-pyridin-3-yl]-N-(2-hydroxyethyl)-benzamide | 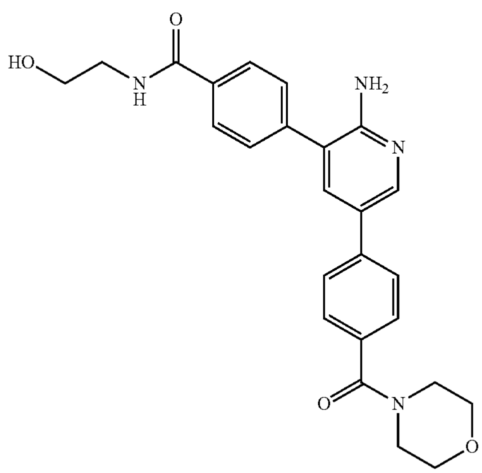 [SMILES: Nc1ncc(-c2ccc(C(=O)N3CCOCC3)cc2)cc1-c1ccc(C(=O)NCCO)cc1] | 447 | 400 MHz, DMSO-$d_6$): δ 8.53-8.50 (m, 1H), 8.38 (d, 1H, J = 2.0 Hz), 7.98 (d, 2H, J = 8.0 Hz), 7.74 (d, 2H, J = 8.0 Hz), 7.71 (d, 1H, J = 2.0 Hz), 7.64 (d, 2H, J = 8.0 Hz), 7.46 (d, 2H, J = 8.0 Hz), 5.96 (bs, 2H), 4.76 (t, 1H, J = 5.48 Hz), 3.61-3.51 (m, 10H) & 3.39-3.36 (m, 2H) |
| 76 | 4-[2-amino-3-(2-methoxypyridin-5-yl)pyridin-5-yl]benzene sulfonamide | 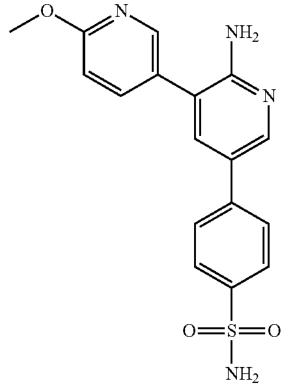 [SMILES: COc1ccc(-c2cc(-c3ccc(S(N)(=O)=O)cc3)cnc2N)cn1] | 356 | 300 MHz, DMSO-$d_6$: δ 8.39 (d, 1H, J = 2.4 Hz), 8.30 (dd, 1H, J = 2.4 & 0.9 Hz), 7.84 (m, 5H), 7.71 (d, 1H, J = 2.4 Hz), 7.25 (bs, 2H), 6.92 (dd, 1H, J = 8.4 & 0.9 Hz), 5.89 (bs, 2H) & 3.92 (s, 3H) |

TABLE 2-continued

| N° | Chemical name | Structure | MS m/z [M + H]⁺ | ¹H NMR |
|---|---|---|---|---|
| 80 | 4-[2-amino-3-(4-benzamido)pyridin-5-yl]benzamide | 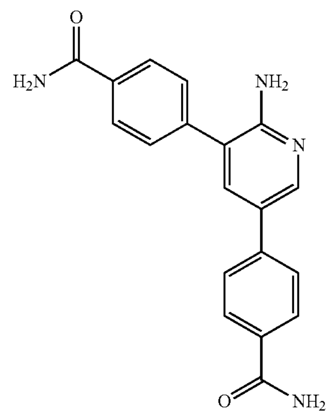 [SMILES: NC(=O)c1ccc(-c2cnc(N)c(-c3ccc(C(N)=O)cc3)c2)cc1] | 332 | ¹H NMR (300 MHz, CD₃OD): δ 8.33 (d, 1H, J = 2.4 Hz), 8.04-7.93 (m, 4H), 7.78 (d, 1H, J = 2.4 Hz) & 7.74-7.63 (m, 4H) |
| 82 | {4-[2-amino-3-(2-methoxypyridin-5-yl)pyridin-5-yl]phenyl}(4-methylpiperazin-1-yl)methanone | 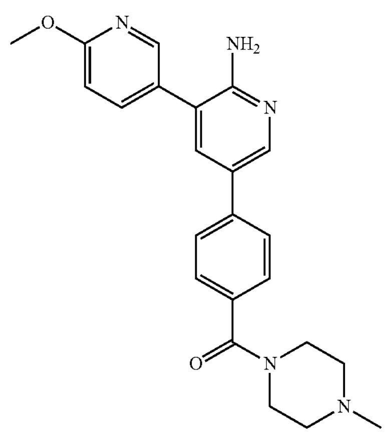 | 403 | 300 MHz, CDCl₃: δ 8.32 (d, 1H, J = 2.1 Hz), 8.26 (d, 1H, J = 1.8 Hz), 7.70 (dd, 1H, J = 8.7 & 2.4 Hz), 7.61-7.39 (m, 5H), 6.85 (d, 1H, J = 8.7 Hz), 4.69 (bs, 2H), 3.97 (s, 3H), 3.89-3.37 (m, 4H), 2.42 (bs, 4H) & 2.31 (s, 3H) |
| 84 | 4-[2-amino-3-(2-methoxypyridin-5-yl)pyridin-5-yl]-N-[4-(aminomethyl)-thiazol-2-yl]benzamide | 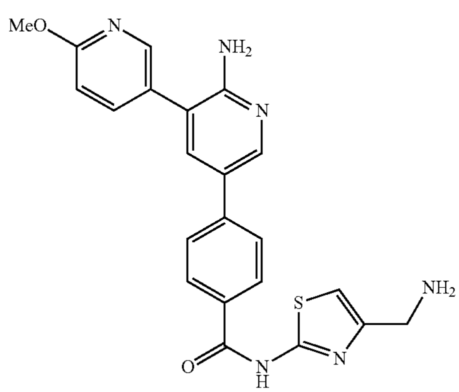 [SMILES: COc1ccc(-c2cc(-c3ccc(C(=O)Nc4nc(CN)cs4)cc3)cnc2N)cn1] | 432 | 300 MHz, CD₃OD: δ 8.51 (d, 1H, J = 2.4 Hz), 8.41 (d, 1H, J = 2.1 Hz), 8.24 (d, 2H, J = 8.4 Hz), 7.96 (d, 1H, J = 2.4 Hz), 7.91 (d, 2H, J = 8.4 Hz), 7.85 (d, 1H, J = 2.4 Hz), 7.11-6.96 (m, 2H), 4.05 (s, 3H) & 3.96 (s, 2H) |

TABLE 2-continued

| N° | Chemical name | Structure | MS m/z [M + H]⁺ | ¹H NMR |
|---|---|---|---|---|
| 86 | {4-[2-amino-3-(4-(trifluoro methyl)phenyl)-pyridin-5-yl]phenyl}-(morpholino)-methanone | 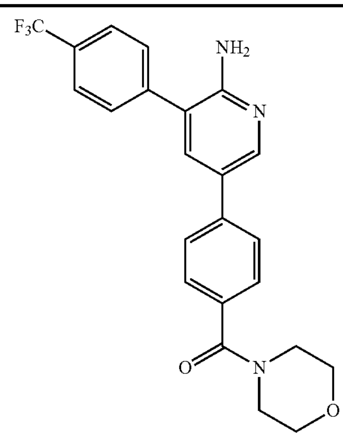 | 427 | ¹H NMR (400 MHz, DMSO-$d_6$): δ 8.40 (d, 1H, J = 2.4 Hz), 7.84-7.71 (m, 7H), 7.47-7.43 (m, 2H), 5.87 (bs, 2H), 3.63-3.60 (m, 4H), 3.52 (bs, 4H) |

The following compounds listed in Table 3 below were also prepared using an analogous procedure to the procedure of Scheme 2 described above:

TABLE 3

| N° | Chemical name | Structure | MS m/z [M + H]⁺ | ¹H NMR |
|---|---|---|---|---|
| 19 | 3-(2-methoxy pyridin-3-yl)-5-[4-(methyl sulfonyl phenyl] pyridin-2-amine | 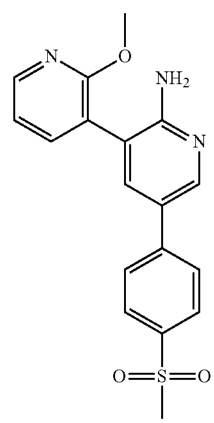 [SMILES: COc1ncccc1-c1cc(-c2ccc(S(C)(=O)=O)cc2)cnc1N] | 356 | 400 MHz, DMSO-$d_6$: δ 8.44 (d, 1H, J = 2.4 Hz), 8.25 (dd, 1H, J = 5.2 & 1.6 Hz), 7.92 (s, 4H), 7.73 (m, 2H), 7.11 (dd, 1H, J = 7.2 & 5.2 Hz), 5.88 (bs, 2H), 3.88 (s, 3H) & 3.23 (s, 3H) |
| 20 | 5-[4-(methyl sulfonyl)phenyl]-3-(pyridin-3-yl) pyridin-2-amine | 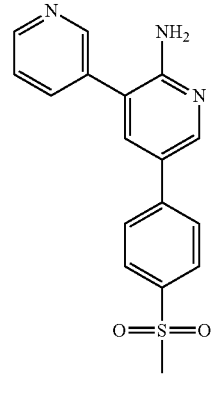 [SMILES: CS(=O)(=O)c1ccc(-c2cnc(N)c(-c3cccnc3)c2)cc1] | 326 | 400 MHz, DMSO-$d_6$: δ 8.73 (dd, 1H, J = 2.4 & 0.8 Hz), 8.60 (dd, 1H, J = 4.8 & 1.6 Hz), 8.46 (d, 1H, J = 2.4 Hz), 7.95 (m, 5H), 7.80 (d, 1H, J = 2.4 Hz), 7.50 (ddd, 1H, J = 7.6, 4.8 & 0.8 Hz), 6.12 (bs, 2H) & 3.23 (s, 3H) |

TABLE 3-continued

| N° | Chemical name | Structure | MS m/z [M + H]+ | 1H NMR |
|---|---|---|---|---|
| 25 | 4-{2-amino-5-[4-(methylsulfonyl)-phenyl]pyridin-3-yl}benzonitrile | 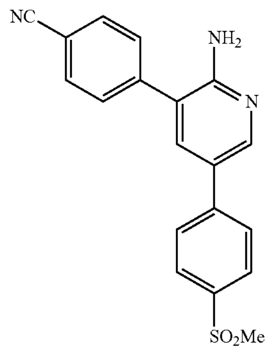 [SMILES: CS(=O)(=O)c1ccc(-c2cnc(N)c(-c3ccc(C#N)cc3)c2)cc1] | 350 | 400 MHz, DMSO-d6: δ 8.47 (d, 1H, J = 2.4 Hz), 7.92-7.98 (m, 6H), 7.81-7.76 (m, 3H), 6.21 (bs, 2H) & 3.24 (s, 3H) |
| 26 | 3-{2-amino-5-[4-(methylsulfonyl)-phenyl]pyridin-3-yl}benzonitrile | 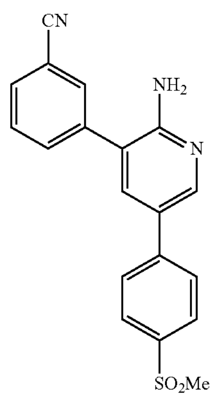 [SMILES: CS(=O)(=O)c1ccc(-c2cnc(N)c(-c3cccc(C#N)c3)c2)cc1] | 350 | 400 MHz, DMSO-d6: δ 8.47 (d, 1H, J = 2.4 Hz), 8.01-7.85 (m, 7H), 7.82 (d, 1H, J = 2.4 Hz), 7.70 -7.66 (m, 1H), 6.23 (bs, 2H) & 3.24 (s, 3H) |
| 28 | 4-{2-amino-5-[4-(methylsulfonyl)phenyl]pyridin-3-yl} benzamide | 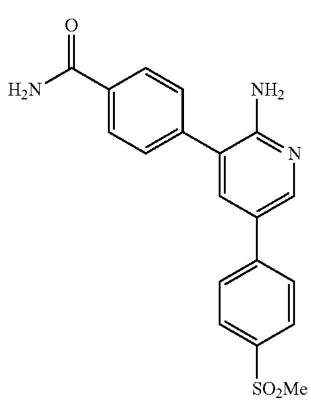 [SMILES: CS(=O)(=O)c1ccc(-c2cnc(N)c(-c3ccc(C(N)=O)cc3)c2)cc1] | 368 | 400 MHz, DMSO-d6: δ 8.45 (d, 1H, J = 2.4 Hz), 8.07 (s, 1H), 8.02-7.92 (m, 6H), 7.78 (d, 1H, J = 2.4 Hz), 7.64 (d, 2H, J = 8.4 Hz), 7.44 (bs, 1H), 6.11 (bs, 2H) & 3.24 (s, 3H) |
| 29 | 4-{2-amino-5-[4-(methylsulfonyl)-phenyl]pyridin-3-yl}-N-methyl benzamide | 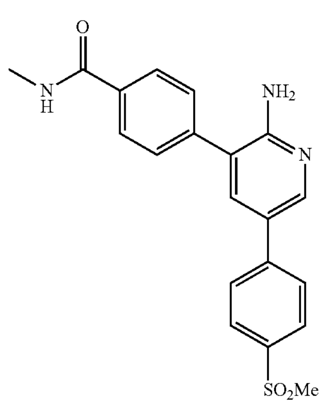 [SMILES: CNC(=O)c1ccc(-c2cc(-c3ccc(S(C)(=O)=O)cc3)cnc2N)cc1] | 382 | 400 MHz, DMSO-d6: δ 8.45 (m, 2H), 7.94 (m, 6H), 7.77 (d, 1H, J = 2.0 Hz), 7.64 (d, 1H, J = 8.4 Hz), 6.03 (bs, 2H), 3.30 (bs, 1H), 3.23 (s, 3H) & 2.83 (d, 3H, J = 4.4 Hz) |

TABLE 3-continued

| N° | Chemical name | Structure | MS m/z [M + H]⁺ | ¹H NMR |
|---|---|---|---|---|
| 30 | 3-(H-imidazo[1,2-a]pyridin-6-yl)-5-[4-(methyl sulfonyl)phenyl] pyridin-2-amine | 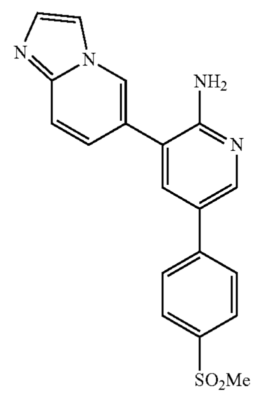 [SMILES: CS(=O)(=O)c1ccc(-c2cnc(N)c(-c3ccc4nccn4c3)c2)cc1] | 365 | 400 MHz, DMSO-d$_6$: δ 8.71 (s, 1H), 8.47 (d, 1H, J = 2.4 Hz), 7.92-7.98 (m, 5H), 7.86 (d, 1H, J = 2.4 Hz), 7.77-7.62 (m, 2H), 7.35 (dd, 1H, J = 9.6 & 2.4 Hz), 6.26 (bs, 2H) & 3.24 (s, 3H) |
| 31 | 3-(2-methoxy pyrimidin-5-yl)-5-[4-(methylsulfonyl) phenyl]pyridin-2-amine | 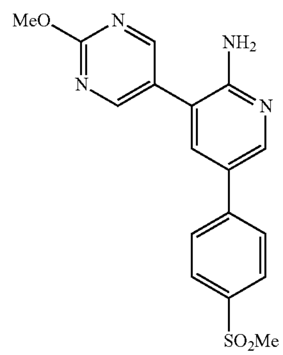 [SMILES: COc1ncc(-c2cc(-c3ccc(S(C)(=O)=O)cc3)cnc2N)cn1] | 357 | 400 MHz, DMSO-d$_6$: δ 8.72 (s, 2H), 8.46 (d, 1H, J = 2.4 Hz), 7.97-7.92 (m, 4H), 7.82 (d, 1H, J = 2.4 Hz), 6.28 (bs, 2H), 3.98 (s, 3H) & 3.24 (s, 3H) |
| 32 | 5-[4-(methyl sulfonyl)phenyl]-3-(quinoxalin-7-yl) pyridin-2-amine | 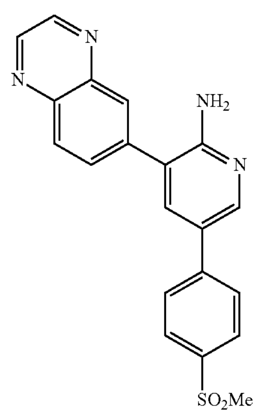 [SMILES: CS(=O)(=O)c1ccc(-c2cnc(N)c(-c3ccc4nccnc4c3)c2)cc1] | 377 | 400 MHz, DMSO-d$_6$: δ 9.01 (d, 1H, J = 2.0 Hz), 8.99 (d, 1H, J = 2.0 Hz), 8.51 (d, 1H, J = 2.0 Hz), 8.26 (d, 1H, J = 2.0 Hz), 8.20 (d, 1H, J = 8.4 Hz), 8.06-7.93 (m, 6H), 6.28 (bs, 2H) & 3.25 (s, 3H) |
| 33 | 3-(furan-3-yl)-5-[4-(methylsulfonyl) phenyl]pyridin-2-amine | 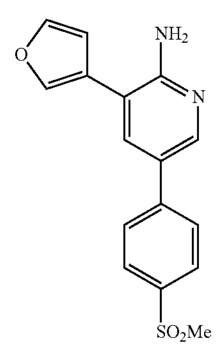 [SMILES: CS(=O)(=O)c1ccc(-c2cnc(N)c(-c3ccoc3)c2)cc1] | 315 | 400 MHz, DMSO-d$_6$: δ 8.4 (d, 1H, J = 2.4 Hz), 8.11 (d, 1H, J = 0.8 Hz), 7.97-7.91 (m, 5H), 7.82 (m, 1H), 7.00 (m, 1H), 6.10 (bs, 2H) & 3.23 (s, 3H) |

TABLE 3-continued

| N° | Chemical name | Structure | MS m/z [M + H]+ | 1H NMR |
|---|---|---|---|---|
| 34 | 3-[4-(5-methyl-1,3,4-oxadiazol-2-yl)phenyl]-5-[4-(methylsulfonyl)phenyl]pyridin-2-amine | 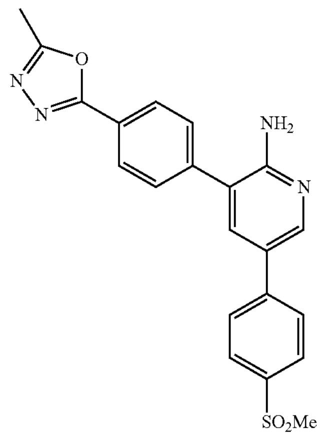 [SMILES: Cc1nnc(-c2ccc(-c3cc(-c4ccc(S(C)(=O)=O)cc4)cnc3N)cc2)o1] | 407 | 400 MHz, DMSO-d$_6$: δ 8.47 (d, 1H, J = 2.4 Hz), 8.07 (d, 2H, J = 8.4 Hz), 7.99-7.92 (m, 4H), 7.83 (d, 1H, J = 2.4 Hz), 7.79 (d, 2H, J = 8.4 Hz), 6.20 (bs, 2H), 3.24 (s, 3H) & 2.62 (s, 3H) |
| 35 | 3-(3-chloro-2-methoxypyridin-5-yl)-5-[4-(methyl sulfonyl) phenyl] pyridin-2-amine | 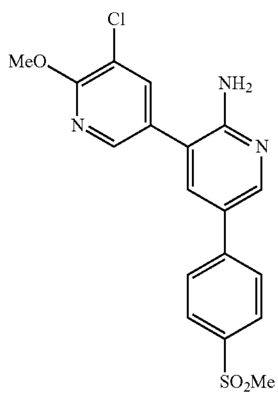 [SMILES: COc1ncc(-c2cc(-c3ccc(S(C)(=O)=O)cc3)cnc2N)cc1Cl] | 390 | 400 MHz, DMSO-d$_6$: δ 8.44 (d, 1H, J = 2.4 Hz), 8.27 (d, 1H, J = 2.4 Hz), 7.91 (s, 4H), 7.83 (d, 1H, J = 2.4 Hz), 7.74 (d, 1H, J = 2.4 Hz), 6.09 (bs, 2H), 3.85 (s, 3H) & 3.22 (s, 3H) |
| 36 | 5-[4-(methyl sulfonyl)phenyl]-3-[3-(trifluoro methoxy)phenyl] pyridin-2-amine | 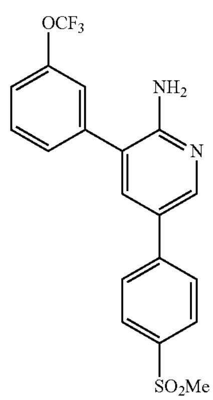 [SMILES: CS(=O)(=O)c1ccc(-c2cnc(N)c(-c3cccc(OC(F)(F)F)c3)c2)cc1] | 409 | 400 MHz, DMSO-d$_6$: δ 8.46 (d, 1H, J = 2.0 Hz), 7.98-7.91 (m, 4H), 7.79 (d, 1H, J = 2.0 Hz), 7.63-7.61 (m, 2H), 7.54 (s, 1H), 7.41 (s, 1H), 6.15 (bs, 2H) & 3.24 (s, 3H) |
| 37 | 5-[4-(methyl sulfonyl) phenyl]-3-[4-(trifluoro methoxy) phenyl]pyridin-2-amine | 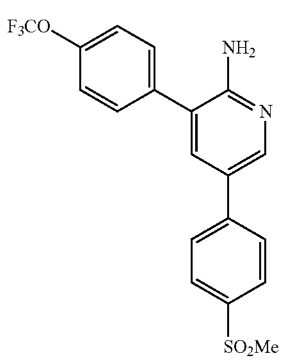 [SMILES: CS(=O)(=O)c1ccc(-c2cnc(N)c(-c3ccc(OC(F)(F)F)cc3)c2)cc1] | 409 | 400 MHz, DMSO-d$_6$: δ 8.45 (d, 1H, J = 2.4 Hz), 7.97-7.91 (m, 4H), 7.78 (d, 1H, J = 2.4 Hz), 7.68 (d, 2H, J = 8.4 Hz), 7.48 (d, 2H, J = 8.4 Hz), 6.11 (bs, 2H) & 3.24 (s, 3H) |

TABLE 3-continued

| N° | Chemical name | Structure | MS m/z [M + H]+ | 1H NMR |
|---|---|---|---|---|
| 38 | 5-[4-(methyl sulfonyl)phenyl]-3-[2-(pyrrolidin-1-yl)pyridin-5-yl]pyridin-2-amine | 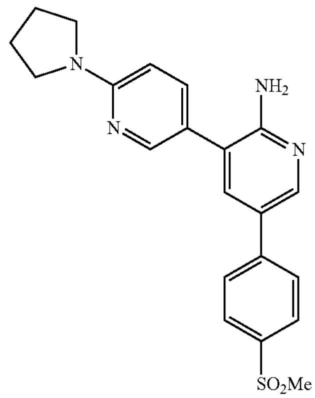 [SMILES: CS(=O)(=O)c1ccc(-c2cnc(N)c(-c3ccc(N4CCCC4)nc3)c2)cc1] | 395 | 400 MHz, DMSO-d6: δ 8.37 (d, 1H, J = 2.4 Hz), 8.22 (d, 1H, J = 2.4 Hz), 7.93 (s, 4H), 7.68-7.64 (m, 2H), 6.55 (d, 1H, J = 8.8 Hz), 5.97 (bs, 2H), 3.44 (t, 4H, J = 6.4 Hz), 3.24 (s, 3H), 1.97 (t, 4H, J = 6.4 Hz) |
| 39 | 3-[2-chloro-4-(trifluoromethyl)phenyl]-5-[4-(methyl sulfonyl)phenyl]pyridine-2-amine | 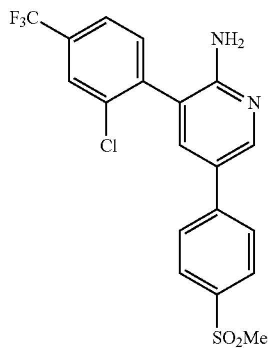 [SMILES: CS(=O)(=O)c1ccc(-c2cnc(N)c(-c3ccc(C(F)(F)F)cc3Cl)c2)cc1] | 427 | 400 MHz, DMSO-d6: δ 8.51 (d, 1H, J = 2.4 Hz), 8.01 (s, 1H), 7.92 (s, 4H), 7.82 (d, 1H, J = 8.0 Hz), 7.76 (d, 1H, J = 2.4 Hz), 7.67 (d, 1H, J = 8.0 Hz), 6.13 (bs, 2H) & 3.23 (s, 3H) |
| 40 | 3-(3-methoxy pyridin-4-yl)-5-[4-(methylsulfonyl)phenyl]pyridin-2-amine | 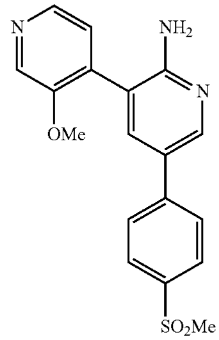 [SMILES: COc1cnccc1-c1cc(-c2ccc(S(C)(=O)=O)cc2)cnc1N] | 356 | 400 MHz, DMSO-d6: δ 8.48 (s, 1H), 8.46 (d, 1H, J = 2.4 Hz), 8.30 (d, 1H, J = 4.8 Hz), 7.92 (s, 4H), 7.72 (d, 1H, J = 2.4 Hz), 7.33 (d, 1H, J = 4.8 Hz), 5.98 (bs, 2H), 3.90 (s, 3H) & 3.23 (s, 3H) |
| 41 | 5-[4-(methyl sulfonyl)phenyl]-3-(2-morpholino pyridin-5-yl)pyridin-2-amine | 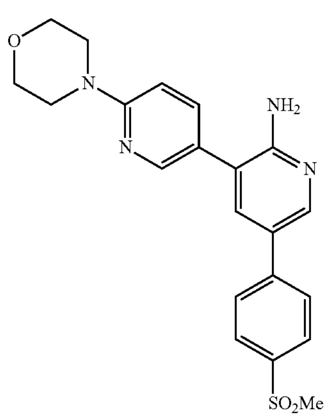 | 411 | 400 MHz, DMSO-d6: δ 8.38 (d, 1H, J = 2.4 Hz), 8.28 (d, 1H, J = 2.4 Hz), 7.94-7.89 (m, 4H), 7.74-7.69 (m, 2H), 6.94 (d, 1H, J = 8.8 Hz), 6.01 (bs, 2H), 3.71 (t, 4H, J = 5.2 Hz), 3.50 (t, 4H, J = 5.2 Hz) & 3.22 (s, 3H) |

TABLE 3-continued

| N° | Chemical name | Structure | MS m/z [M + H]+ | 1H NMR |
|---|---|---|---|---|
| 42 | 3-[2-(trifluoro methyl)pyridin-4-yl]-5-[4-(methyl sulfonyl)phenyl] pyridin-2-amine | 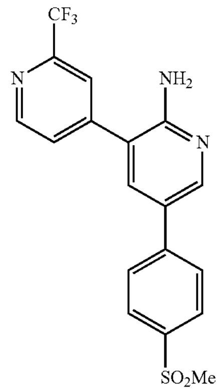 [SMILES: CS(=O)(=O)c1ccc(-c2cnc(N)c(-c3ccnc(C(F)(F)F)c3)c2)cc1] | 394 | 400 MHz, DMSO-d$_6$: δ 8.84 (d, 1H, J = 4.8 Hz), 8.52 (d, 1H, J = 2.4 Hz), 8.06 (s, 1H), 7.98-7.93 (m, 6H), 6.42 (bs, 2H) & 3.24 (s, 3H) |
| 43 | 3-(2-methylpyridin-5-yl)-5-[4-(methyl sulfonyl)phenyl] pyridin-2-amine | 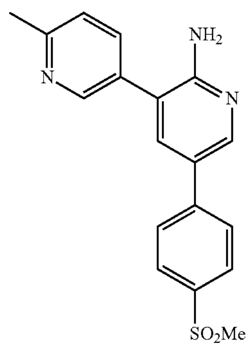 [SMILES: Cc1ccc(-c2cc(-c3ccc(S(C)(=O)=O)cc3)cnc2N)cn1] | 340 | 400 MHz, DMSO-d$_6$: δ 8.59 (d, 1H, J = 2.4 Hz), 8.44 (d, 1H, J = 2.4 Hz), 7.97-7.91 (m, 4H), 7.84 (dd, 1H, J = 8.0 & 2.28 Hz), 7.76 (d, 1H, J = 2.4 Hz), 7.37 (d, 1H, J = 8.0 Hz), 6.13 (bs, 2H), 3.24 (s, 3H) & 2.53 (s, 3H) |
| 44 | 3-[2-(trifluoro methyl)pyridin-5-yl]-5-[4-(methyl sulfonyl)phenyl] pyridin-2-amine | 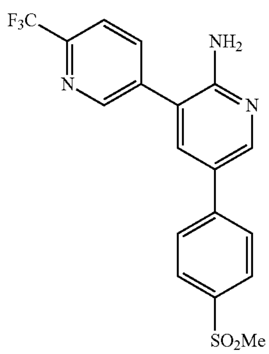 | 394 | 400 MHz, DMSO-d$_6$: δ 8.91 (d, 1H, J = 1.6 Hz), 8.50 (d, 1H, J = 2.4 Hz), 8.24 (dd, 1H, J = 8.0 & 1.6 Hz), 8.00-7.88 (m, 6H), 6.35 (bs, 2H) & 3.23 (s, 3H) |
| 45 | 3-{4-[2-(pyrrolidin-1-yl)ethoxy] phenyl}-5-[4-(methylsulfonyl) phenyl] pyridin-2-amine | 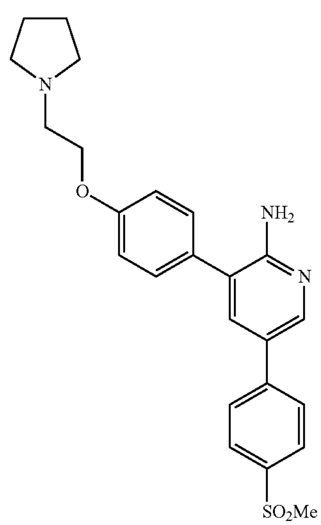 [SMILES: CS(=O)(=O)c1ccc(-c2cnc(N)c(-c3ccc(OCCN4CCCC4)cc3)c2)cc1] | 438 | 400 MHz, DMSO-d$_6$: δ 8.38 (s, 1H), 7.92 (s, 4H), 7.68 (s, 1H), 7.45 (d, 2H, J = 8.4 Hz), 7.05 (d, 2H, J = 8.4 Hz), 5.93 (bs, 2H), 4.12 (t, 2H, J = 5.6 Hz), 3.22 (s, 3H), 2.85 (s, 2H), 2.55 (s, 4H) & 1.70 (s, 4H) |

TABLE 3-continued

| N° | Chemical name | Structure | MS m/z [M + H]+ | 1H NMR |
|---|---|---|---|---|
| 46 | 5-[4-(methyl sulfonyl)phenyl]-3-(4-morpholino phenyl)pyridin-2-amine | 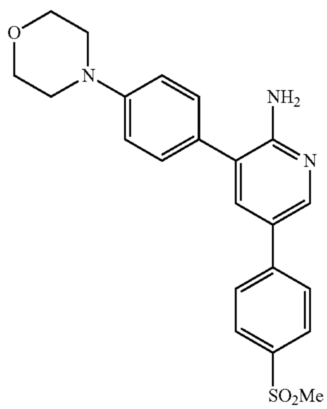 [SMILES: CS(=O)(=O)c1ccc(-c2cnc(N)c(-c3ccc(N4CCOCC4)cc3)c2)cc1] | 410 | 400 MHz, DMSO-d6: δ 8.36 (d, 1H, J = 2.4 Hz), 7.94-7.92 (m, 4H), 7.67 (d, 1H, J = 2.4 Hz), 7.41 (d, 2H, J = 8.8 Hz), 7.06 (d, 2H, J = 8.8 Hz), 5.90 (bs, 2H), 3.76 (t, 4H, J = 4.8 Hz), 3.23 (s, 3H) & 3.17 (t, 4H, J = 9.6 Hz) |
| 47 | 3-[4-(1H-pyrazol-1-yl)phenyl]-5-[4-(methylsulfonyl)phenyl]pyridin-2-amine | 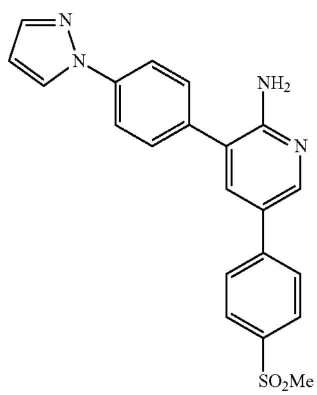 [SMILES: CS(=O)(=O)c1ccc(-c2cnc(N)c(-c3ccc(-n4cccn4)cc3)c2)cc1] | 391 | 400 MHz, DMSO-d6: δ 8.58 (d, 1H, J = 2.4 Hz), 8.43 (d, 1H, J = 2.4 Hz), 7.97-7.91 (m, 6H), 7.78 (d, 2H, J = 2.0 Hz), 7.68-7.65 (m, 2H), 6.57 (t, 1H, J = 4.0 Hz), 6.08 (bs, 2H) & 3.23 (s, 3H). |
| 55 | 5-{2-amino-5-[4-(methylsulfonyl)-phenyl]pyridin-3-yl}pyrimidin-2-amine | 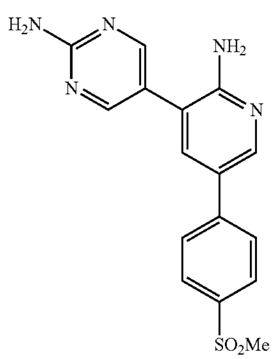 [SMILES: CS(=O)(=O)c1ccc(-c2cnc(N)c(-c3cnc(N)nc3)c2)cc1] | 342 | 400 MHz, DMSO-d6: δ 8.38 (d, 1H, J = 2.4 Hz), 8.36 (s, 2H), 7.95-7.92 (m, 4H), 7.72 (d, 1H, J = 2.4 Hz), 6.79 (bs, 2H), 6.15 (s, 2H) & 3.23 (s, 3H) |
| 56 | 3-{2-amino-5-[4-(methylsulfonyl)phenyl]pyridin-3-yl}benzamide | 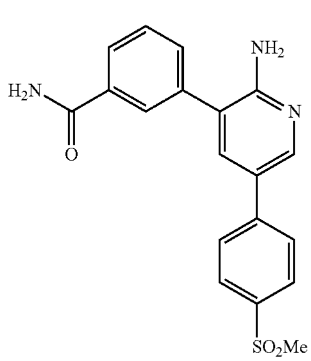 [SMILES: CS(=O)(=O)c1ccc(-c2cnc(N)c(-c3cccc(C(N)=O)c3)c2)cc1] | 368 | 400 MHz, DMSO-d6: δ 8.45 (d, 1H, J = 2.0 Hz), 8.06 (s, 1H), 8.00-7.87 (m, 5H), 7.79 (d, 1H, J = 1.6 Hz), 7.70 (d, 1H, J = 8.4 Hz), 7.58 (d, 1H, J = 8.0 Hz), 7.44 (s, 1H), 6.09 (bs, 2H) & 3.24 (s, 3H) |

TABLE 3-continued

| N° | Chemical name | Structure | MS m/z [M + H]+ | 1H NMR |
|---|---|---|---|---|
| 57 | 3-(6-methoxy-2-methylpyridin-3-yl)-5-[4-(methyl sulfonyl)phenyl]pyridin-2-amine | 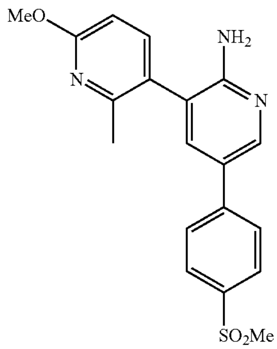 [SMILES: COc1ccc(-c2cc(-c3ccc(S(C)(=O)=O)cc3)cnc2N)c(C)n1] | 370 | 400 MHz, DMSO-d6: δ 8.44 (d, 1H, J = 2.4 Hz), 7.91 (s, 4H), 7.66 (d, 1H, J = 2.4 Hz), 7.52 (d, 1H, J = 8.4 Hz), 6.73 (d, 1H, J = 8.4 Hz), 5.95 (bs, 2H), 3.88 (s, 3H), 3.22 (s, 3H) & 2.26 (s, 3H) |
| 58 | 3-(isoquinolin-5-yl)-5-[4-(methyl sulfonyl)phenyl]-pyridin-2-amine | 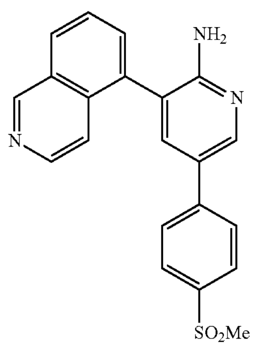 [SMILES: CS(=O)(=O)c1ccc(-c2cnc(N)c(-c3cccc4cnccc34)c2)cc1] | 376 | 400 MHz, DMSO-d6: δ 9.41 (s, 1H), 8.57 (d, 1H, J = 2.4 Hz), 8.48 (d, 1H, J = 5.6 Hz), 8.23-8.20 (m, 1H), 7.96 (d, 1H, J = 8.4 Hz), 7.91 (d, 2H, J = 8.4 Hz), 7.81-7.79 (m, 3H), 7.41 (d, 1H, J = 5.6 Hz), 5.89 (bs, 2H) & 3.23 (s, 3H) |
| 59 | 5-[4-(methyl sulfonyl)phenyl]-3-(quinolin-6-yl)pyridin-2-amine | 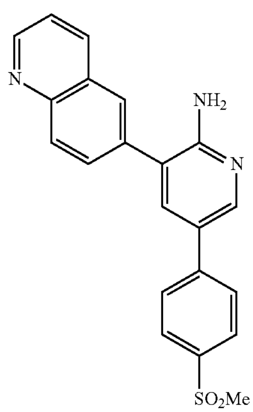 [SMILES: CS(=O)(=O)c1ccc(-c2cnc(N)c(-c3ccc4ncccc4c3)c2)cc1] | 376 | 400 MHz, DMSO-d6: δ 8.94 (d, 1H, J = 3.6 Hz), 8.49 (d, 1H, J = 2.0 Hz), 8.43 (d, 1H, J = 8.4 Hz), 8.17 (s, 1H), 8.12 (d, 1H, J = 8.4 Hz), 7.99-7.88 (m, 6H), 7.60-7.57 (m, 1H), 6.20 (bs, 2H) & 3.24 (s, 3H) |
| 65 | 5-[4-(methyl sulfonyl)phenyl]-3-p-tolylpyridin-2-amine | 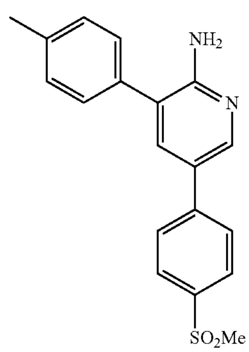 [SMILES: Cc1ccc(-c2cc(-c3ccc(S(C)(=O)=O)cc3)cnc2N)cc1] | 338 | 1H NMR (400 MHz, DMSO-d6): δ 8.40 (d, 1H, J = 2.4 Hz), 7.93 (s, 4H), 7.69 (d, 1H, J = 2.4 Hz), 7.45-7.42 (m, 2H), 7.32-7.30 (m, 2H), 3.22 (s, 3H) & 2.37 (s, 3H) |

TABLE 3-continued

| N° | Chemical name | Structure | MS m/z [M + H]+ | 1H NMR |
|---|---|---|---|---|
| 69 | {5-[2-amino-5-(4-(methylsulfonyl)-phenyl)pyridin-3-yl] pyridin-2-yl}methanol | 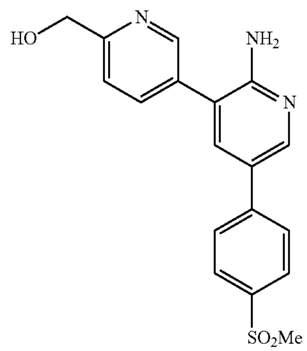 [SMILES: CS(=O)(=O)c1ccc(-c2cnc(N)c(-c3ccc(CO)nc3)c2)cc1] | 356 | 400 MHz, DMSO-d$_6$: δ 8.63 (s, 1H), 8.45 (s, 1H), 7.97-7.92 (m, 5H), 7.79 (s, 1H), 7.57 (d, 1H, J = 8.0 Hz), 6.15 (bs, 2H), 5.51 (t, 1H, J = 1.2 Hz), 4.63 (d, 2H, J = 5.6 Hz) & 3.24 (d, 3H, J = 0.8 Hz) |
| 70 | 3-(2-methylbenzo[d]-thiazol-5-yl)-5-[4-(methylsulfonyl) phenyl]pyridin-2-amine | 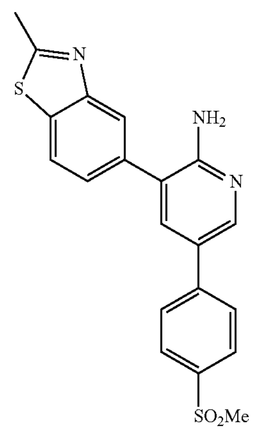 [SMILES: Cc1nc2cc(-c3cc(-c4ccc(S(C)(=O)=O)cc4)cnc3N)ccc2s1] | 396 | 400 MHz, DMSO-d$_6$: δ 8.45 (d, 1H, J = 2.4 Hz), 8.20 (d, 1H, J = 1.6 Hz), 7.94-7.91 (m, 5H), 7.82 (d, 1H, J = 2.4 Hz), 7.63 (dd, 1H, J = 7.2 & 1.6 Hz), 6.12 (bs, 2H), 3.24 (s, 3H) & 2.84 (s, 3H) |
| 75 | N-{4-[2-amino-5-(4-(methylsulfonyl) phenyl)pyridin-3-yl]phenyl}-2-(dimethylamino) acetamide | 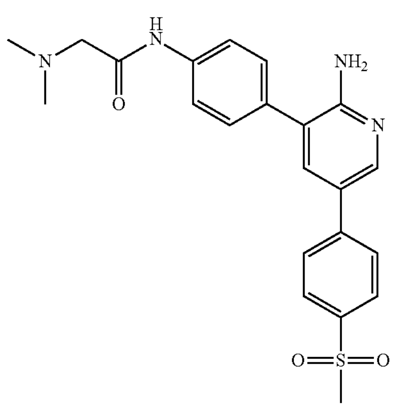 [SMILES: CN(C)CC(=O)Nc1ccc(-c2cc(-c3ccc(S(C)(=O)=O)cc3)cnc2N)cc1] | 425 | 400 MHz, DMSO-d$_6$): δ 9.89 (s, 1H), 8.40 (d, 1H, J = 2.0 Hz), 7.96-7.91 (m, 4H), 7.80 (d, 2H, J = 8.4 Hz), 7.71 (d, 1H, J = 2.0 Hz), 7.48 (d, 2H, J = 8.4 Hz), 5.99 (bs, 2H), 3.24 (s, 3H), 3.12 (s, 2H) & 3.30 (s, 6H) |
| 77 | 3-(2-fluoropyridin-5-yl)-5-[4-(methylsulfonyl)-phenyl]pyridin-2-amin | 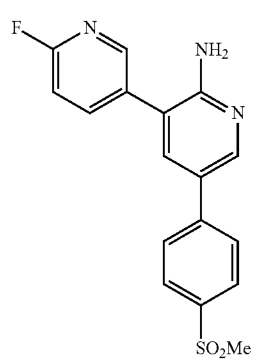 [SMILES: CS(=O)(=O)c1ccc(-c2cnc(N)c(-c3ccc(F)nc3)c2)cc1] | 344 | 400 MHz, DMSO-d$_6$: δ 8.46 (d, 1H, J = 2.4 Hz), 8.37 (d, 1H, J = 2.4 Hz), 8.12 (td, 1H, J = 8.4 & 2.8 Hz), 7.94 (m, 4H), 7.80 (d, 1H, J = 2.4 Hz), 7.29 (dd, 1H, J = 8.8 & 2.8 Hz), 6.16 (bs, 2H), 3.23 (s, 3H) |

TABLE 3-continued

| N° | Chemical name | Structure | MS m/z [M + H]+ | 1H NMR |
|---|---|---|---|---|
| 78 | 5-[4-(methylsulfonyl)phenyl]-3-[2-(methylsulfonyl)-pyridin-5-yl]pyridin-2-amine | 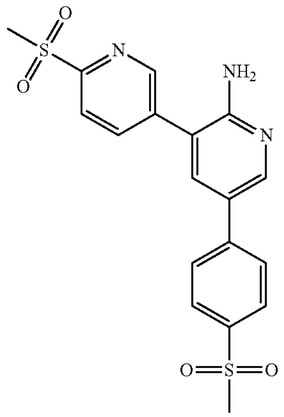 [SMILES: CS(=O)(=O)c1ccc(-c2cnc(N)c(-c3ccc(S(C)(=O)=O)nc3)c2)cc1] | 403 | 400 MHz, DMSO-d6): δ 8.93 (dd, 1H, J = 2.0 and 0.8 Hz), 8.51 (d, 1H, J = 2.4 Hz), 8.31 (dd, 1H, J = 8.0 and 2.0 Hz), 8.12 (dd, 1H, J = 8.0 and 0.8 Hz), 7.98-7.92 (m, 5H), 7.90 (d, 1H, J = 2.4 Hz), 6.33 (bs, 2H) 3.32 (s, 3H) and 3.23 (s, 3H) |
| 79 | N-{5-[2-amino-5-(4-(methylsulfonyl)-phenyl]pyridin-3-yl]pyridin-2-yl}acetamide | 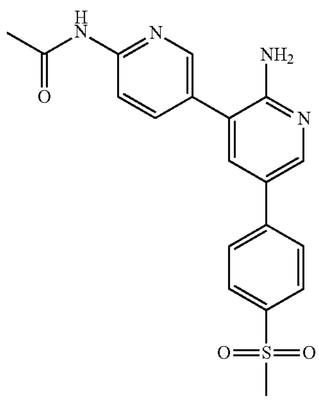 [SMILES: CC(=O)Nc1ccc(-c2cc(-c3ccc(S(C)(=O)=O)cc3)cnc2N)cn1] | 382 | 400 MHz, DMSO-d6): δ 10.57 (bs, 1H), 8.45-8.43 (m, 2H), 8.17 (d, 1H, J = 8.4 Hz), 7.96-7.91 (m, 5H), 7.78 (d, 1H, J = 2.4 Hz), 6.09 (bs, 2H) 3.22 (s, 3H) & 2.13 (s, 3H) |
| 81 | 3-(benzo[c][1,2,5]oxadiazol-5-yl)-5-[4-(methylsulfonyl)phenyl]pyridin-2-amine | 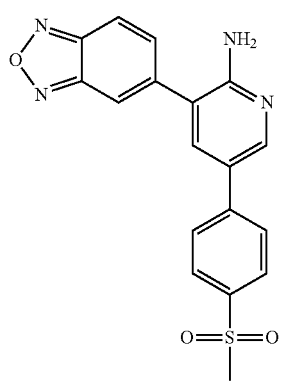 [SMILES: CS(=O)(=O)c1ccc(-c2cnc(N)c(-c3ccc4nonc4c3)c2)cc1] | 366 | 400 MHz, DMSO-d6): δ 8.51 (d, 1H, J = 2.4 Hz), 8.17 (s, 1H), 8.13 (dd, 1H, J = 9.2 & 1.2 Hz), 8.00-7.92 (m, 5H), 7.73 (dd, 1H, J = 9.2 & 1.2 Hz), 6.32 (bs, 2H) & 3.24 (s, 3H) |
| 83 | 3-{2-amino-5-[4-(methylsulfonyl)-phenyl]pyridin-3-yl}-N-(2-hydroxyethyl)benzamide | 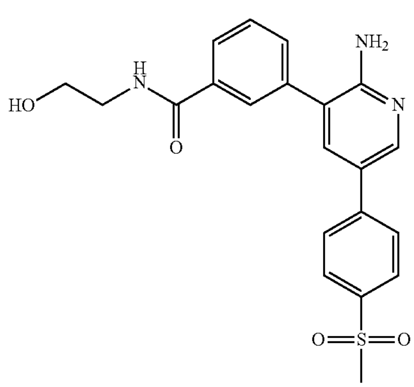 [SMILES: CS(=O)(=O)c1ccc(-c2cnc(N)c(-c3cccc(C(=O)NCCO)c3)c2)cc1] | 412 | 400 MHz, DMSO-d6): δ 8.47 (t, 1H, J = 5.6 Hz), 8.45 (d, 1H, J = 2.8 Hz), 8.01-7.91 (m, 5H), 7.87 (d, 1H, J = 7.6 Hz), 7.78 (d, 1H, J = 2.4 Hz), 7.68 (d, 1H, J = 7.6 Hz), 7.58 (t, 1H, J = 7.6 Hz), 6.04 (bs, 2H), 4.69 (t, 1H, J = 5.6 Hz), 3.53 (q, 2H, J = 6.0 Hz), 3.36 (q, 2H, J = 6.0 Hz) & 3.24 (s, 3H) |

TABLE 3-continued

| N° | Chemical name | Structure | MS m/z [M + H]⁺ | ¹H NMR |
|---|---|---|---|---|
| 85 | 3-[4-(trifluoromethyl)phenyl]-5-[4-(methylsulfonyl)phenyl]pyridin-2-amine | 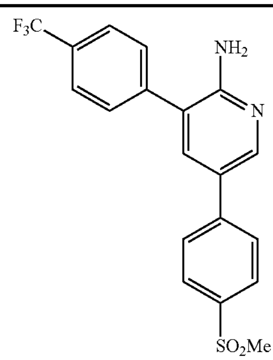 | 392 | ¹H NMR (400 MHz, DMSO-d₆): δ 8.47 (d, 1H, J = 2.4 Hz), 7.97-7.91 (m, 4H), 7.85-7.77 (m, 5H), 6.12 (bs, 2H) & 3.23 (s, 3H) |
| 87 | 3-(3-methylpyridin-5-yl)-5-[4-(methylsulfonyl)phenyl]pyridin-2-amine | 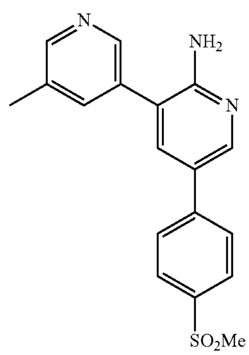 [SMILES: Cc1cncc(-c2cc(-c3ccc(S(C)(=O)=O)cc3)cnc2N)c1] | 340 | ¹H NMR (400 MHz, DMSO-d₆): δ 8.53 (d, 1H, J = 1.6 Hz), 8.46-8.44 (m, 2H), 7.98-7.91 (m, 4H), 7.79-7.78 (m, 2H), 6.18 (bs, 2H), 3.24 (s, 3H) & 2.37 (s, 3H) |

Compound 28 was synthesized as described under Scheme 2 following the protocol below:

3-Bromo-5-[4-(methylsulfonyl)phenyl]pyridin-2-amine

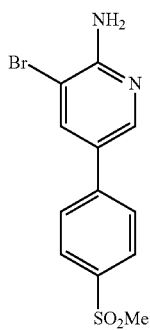

4-Methylsulphonyphenylboronic acid (34.82 g, 0.17 mol) was added to a stirred solution of 5-iodo-3-bromo-2-aminopyridine (47.31 g, 0.16 mol) (commercially available or could be synthesized as described in Zhang et al., 2004, *J. Med. Chem.*, 47(10), 2453-2465) in 1,4-dioxane (470 ml) at RT and purged with N₂ gas for 1 h. Pd[(PPh₃)]₂Cl₂ (7.77 g, 0.01 mol) and an aqueous solution of potassium carbonate (1 M, 160.9 ml, pre-purged with N₂ gas) were added to the reaction mixture, and subsequently heated under reflux for 16 h. The reaction mixture was then cooled to RT, followed by the addition of H₂O (600 ml). The precipitate was filtered, washed with DCM/MeOH (1:1, 300 ml) and dried in vacuo to afford the final compound (30 g, 57.9%) as a white solid. ¹H NMR (400 MHz, DMSO-d₆): δ 8.43 (s, 1H), 8.20 (s, 1H), 7.93 (s, 4H), 6.59 (bs, 2H) and 3.24 (s, 3H). LC-MS APCI: Calculated for C₁₂H₁₁BrN₂O₂S 327; Observed m/z [M+H]⁺ 328.

4-{2-amino-5-[4-(methylsulfonyl)phenyl]pyridin-3-yl}benzamide

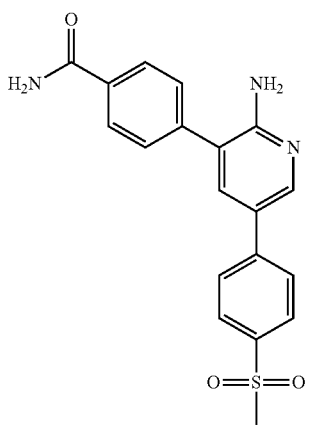 [SMILES: CS(=O)(=O)c1ccc(-c2cnc(N)c(-c3ccc(C(N)=O)cc3)c2)cc1]

Aqueous K₂CO₃ solution (1 M, 0.4 mL) was added to a suspension of 3-bromo-5-[4-(methylsulfonyl)phenyl]pyridin-2-amine obtained as described above (0.15 g, 0.46 mmol), 4-aminocarbonylphenylboronic acid (0.120 g, 0.51 mmol) and Pd[(PPh₃)₃]₄ (0.016 g, 0.02 mmol) in dioxane (5 mL) and DMF (2 mL) under N₂. The reaction mixture was stirred at 120° C. for 14 h, poured onto H₂O (10 mL) and extracted with MeOH/CHCl₃ (1:4) (3×20 mL). The combined organic layers were washed with brine (20 mL), dried over anhydrous MgSO₄ and concentrated in vacuo. The residue was purified by column chromatography on silica gel (5% MeOH/EtOAc) to yield the desired product (0.26 g, 56%). $^1$H NMR (400 MHz, DMSO-d₆): δ 8.45 (d, 1H, J=2.4 Hz), 8.07 (s, 1H), 8.02-7.92 (m, 6H), 7.78 (d, 1H, J=2.4 Hz), 7.64 (d, 2H, J=8.4 Hz), 7.44 (bs, 1H), 6.11 (bs, 2H) and 3.24 (s, 3H). LC-MS APCI: Calculated for $C_{19}H_{17}N_3O_3S$, 367; Observed m/z 368 [M+H]⁺.

The following boronic acid used in the synthesis of compound n° 16, respectively was synthesized as follows:

1-(4-Bromophenylsulfonyl)-4-methylpiperazine

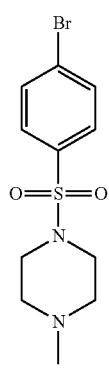

1-methylpiperazine (11.76 g, 117.41 mmol) was added to a solution of 4-[(4-bromobenzene)]sulfonylchloride (3.00 g, 11.74 mmol) in tetrahydrofuran (20 mL). The resulting reaction mixture was stirred at room temperature for 4 h. The solvent was removed and the residue was dissolved in dichloromethane (40 mL). The solution was washed with saturated aqueous sodium hydrogen carbonate (3×10 mL), saturated aqueous sodium chloride (2×10 mL), dried (MgSO₄) and concentrated under reduced pressure to give a colourless solid. The remaining residue was subjected to column chromatography on silica gel using dichloromethane/methanol in a 9.0:1.0 v/v ratio as eluent (3.34 g, 89%); $^1$H NMR (300 MHz, CDCl₃): δ 7.67-7.57 (m, 4H), 3.02 (t, 4H, J=4.8 Hz), 2.45 (t, 4H, J=5.1 Hz) and 2.24 (s, 3H); $^{13}$C NMR (300 MHz, CDCl₃): δ 134.7, 132.4, 129.4, 128.0, 54.1, 46.0 and 45.8. LC-MS APCI: Calculated for $C_{11}H_{15}BrN_2O_2S$, 318; Observed m/z 318 [M]⁺.

4-(4-Methylpiperazin-1-ylsulfonyl)phenylboronic acid

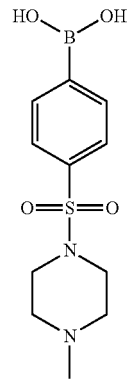

A solution of the starting bromide (1.00 g, 3.13 mmol) in dry tetrahydrofuran (10 mL) was cooled to −78° C., followed by the dropwise addition of nBuLi (1.6 M in hexane, 9.78 mL, 15.66 mmol), whilst maintaining the temperature below −78° C. The resulting reaction mixture was allowed to stir at −78° C. for 1 h. Triisopropyl borate (3.60 mL, 15.66 mmol) was added dropwise at −78° C. and stirred further for 45 min at −78° C. The reaction mixture was allowed to warm to room temperature and stirred for an additional 12 h. A solution of NaOH (0.19 g, 4.70 mmol) in water (10 mL) was added and the reaction was then stirred for a further 12 h, at which time tetrahydrofuran was removed under reduced pressure. The pH was adjusted to 11 with HCl solution (1M) and the resulting solution extracted with ethyl acetate (3×5 mL) to recover the starting material. Then the pH was adjusted to 7 with HCl solution (1M) and the product extracted with ethyl acetate (3×5 mL), dried (MgSO₄) and concentrated under reduced pressure to give a colourless solid which was used without further purification (0.54 g, 61%); $^1$H NMR (400 MHz, DMSO-d₆): δ 8.36 (bs, 2H), 8.02 (d, 2H, J=8.0 Hz), 7.69 (d, 2H, J=8.0 Hz), 2.94 (bs, 4H), 2.57 (bs, 4H) and 2.24 (s, 3H); $^{13}$C NMR (400 MHz, DMSO-d₆): δ 136.0, 134.9, 134.7, 126.3, 53.1, 45.2 and 44.7. LC-MS APCI: Calculated for $C_{11}H_{17}BN_2O_4S$, 284; Observed m/z 284 [M]⁺.

The following compounds listed in Table 4 below were also prepared using an analogous procedure to procedure of Scheme 3 as described above:

TABLE 4

| N° | Chemical name | Structure | MS m/z [M + H]⁺ | $^1$H NMR |
|----|---------------|-----------|-----------------|-----------|
| 72 | 5-[3-fluoro-4-(methylsulfonyl)-phenyl]-3-(2-methoxypyridin-5-yl)pyridin-2-amine | 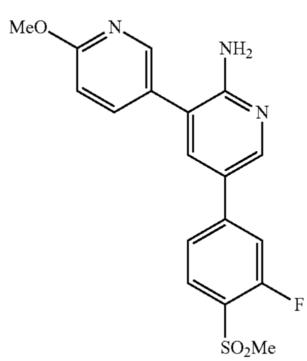 [SMILES: COc1ccc(-c2cc(-c3ccc(S(C)(=O)=O)c(F)c3)cnc2N)cn1] | 374 | 400 MHz, CDCl₃: δ 8.37 (d, 1H, J = 2.4 Hz), 8.28 (dd, 1H, J = 2.4 & 0.8 Hz), 7.99 (m, 1H), 7.71 (dd, 1H, J = 8.4 & 2.4 Hz), 7.56 (d, 1H, J = 2.4 Hz), 7.49 (dd, 1H, J = 8.4 & 2.0 Hz), 7.41 (m, 1H), 6.88 (dd, 1H, J = 8.4 & 0.8 Hz), 4.76 (s, 2H), 4.00 (s, 3H) & 3.24 (s, 3H) |

Compound 72 was synthesized as described under Scheme 3 following the protocol below:

2-Amino-3-(2-methoxypyridin-5-yl)pyridin-5-yl-5-boronic acid

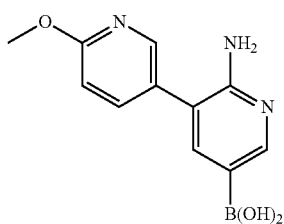 [SMILES: COc1ccc(-c2cc(B(O)O)cnc2N)cn1]

A solution of 5-bromo-3-(2-methoxypyridin-5-yl)pyridin-2-amine (1.04 g, 3.70 mmol) in dry tetrahydrofuran (15 mL) was cooled to −78° C., followed by the dropwise addition of nBuLi (1.6 M in hexane, 5.21 mL, 13.02 mmol) whilst maintaining the temperature below −78° C. The resulting reaction mixture was allowed to stir at −78° C. for 1 h. Triisopropyl borate (3.00 mL, 13.02 mmol) was added dropwise at −78° C. Upon completion of addition, the reaction mixture was stirred for 45 min at −78° C. and allowed to warm to room temperature and stirred for an additional 12 h. A solution of NaOH (0.19 g, 4.70 mmol) in water (15 mL) was added and the reaction was then stirred for 12 h after which time tetrahydrofuran was removed under vacuum. The pH was adjusted to 11 with HCl solution (1M) and the resulting solution extracted with ethyl acetate (3×5 mL) recovering the starting material. The pH was then adjusted to 7 with HCl solution (1M) and the product extracted with ethyl acetate (3×5 mL), dried (MgSO$_4$) and concentrated under reduced pressure to give a colourless solid which was then used without further purification (0.57 g, 63%). $^1$H NMR (400 MHz, DMSO-d$_6$): δ 8.33 (d, 1H, J=2.0 Hz), 8.18 (dd, 1H, J=2.4 and 0.8 Hz), 7.80 (s, 2H), 7.74 (dd, 1H, J=8.8 and 2.8 Hz), 7.67 (d, 1H, J=2.0 Hz), 6.90 (dd, 1H, J=8.4 and 0.8 Hz), 5.86 (s, 2H) and 3.80 (s, 3H). LC-MS APCI: Calculated for C$_{11}$H$_{12}$BN$_3$O$_3$, 245; Observed m/z 245 [M]$^+$.

5-[3-fluoro-4-(methylsulfonyl)phenyl]-3-(2-methoxypyridin-5-yl)pyridin-2-amine

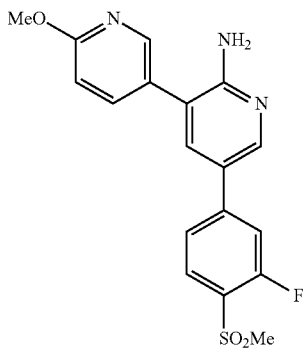 [SMILES: COc1ccc(-c2cc(-c3ccc(S(C)(=O)=O)c(F)c3)cnc2N)cn1]

Aqueous K$_2$CO$_3$ solution (1 M, 0.8 mL) was added to a suspension of 2-Amino-3-(2-methoxypyridin-5-yl)pyridin-5-yl-5-boronic acid obtained as described above (0.170 g, 0.69 mmol), 4-bromo-2-fluoro-1-(methylsulfonyl)benzene (0.195 g, 0.77 mmol) and Pd[(PPh$_3$)]$_4$ (0.027 g, 0.04 mmol) in dioxane (5 mL) and under N$_2$. The reaction mixture was stirred at 90° C. for 20 h, poured onto H$_2$O (10 mL) and extracted with MeOH/CHCl$_3$ (1:4) (3×30 mL). The combined organic layers were washed with brine (30 mL), dried over anhydrous MgSO$_4$ and concentrated in vacuo. The residue was purified by column chromatography on silica gel (1:3 Hex/EtOAc to EtOac) to yield the desired product (0.08 g, 32%). $^1$H NMR (400 MHz, CDCl$_3$): δ 8.37 (d, 1H, J=2.4 Hz), 8.28 (dd, 1H, J=2.4 and 0.8 Hz), 7.99 (m, 1H), 7.71 (dd, 1H, J=8.4 and 2.4 Hz), 7.56 (d, 1H, J=2.4 Hz), 7.49 (dd, 1H, J=8.4 and 2.0 Hz), 7.41 (m, 1H), 6.88 (dd, 1H, J=8.4 and 0.8 Hz), 4.76 (s, 2H), 4.00 (s, 3H) and 3.24 (s, 3H). LC-MS APCI: Calculated for C$_{18}$H$_{16}$FN$_3$O$_3$S, 33; Observed m/z 374 [M+H]$^+$.

EXAMPLE 3

Anti-Malarial in Vitro Efficacy of Aminopyridines According to the Invention The ability of aminopyridine derivatives according to the invention to kill *P. falciparum* parasites and/or to inhibit its proliferation was tested as follows:

Assay 1: The protocol used was as described in the supplemental material to *Fiddock et al.*, 2004, *Nature Reviews Drug Discovery*, (3), p 509.

Assay 2: Compounds were incubated in the presence of 2 or 3% ring stage parasite (*P. falciparum* 3D7 or Dd2) and 0.3% hematocrite in a total assay volume of 50 µL, for 72 hours in a humidified atmosphere at 37° C., 5% O$_2$ and 5% CO$_2$, in Poly-D-lysine coated Cell Carrier Imaging plates (Perkin Elmer). After incubation plates were stained with DAPI (4',6-diamidino-2-phenylindole, Invitrogen) in the presence of Saponin and Triton X-100 (Sigma-Aldrich) and incubated for a further 5 hours at RT in the dark before imaging on the OPERA$^{TM}$ HTS confocal imaging system (Perkin Elmer). The digital images obtained were then analyzed using the PerkinElmer Acapella spot detection software where spots which fulfil the criteria established for a stained parasite are counted. The % inhibition of parasite replication was calculated using DMSO and 2 µM Artemisinin control data. Measured % inhibition and EC$_{50}$ (ng/ml) are reported in Tables 5 & 6 below against different strains of *P. falciparum* K1, NF54 (assay 1) and 3D7, Dd2 (assay 2), respectively.

TABLE 5

| Compound | *P. falciparum* (K1) EC$_{50}$ ng/mL | *P. falciparum* (NF54) EC$_{50}$ ng/mL |
|---|---|---|
| 1 | 14 | 18 |
| 2 | 31 | 41 |
| 10 | 16 | 15 |
| 11 | 55 | 55 |
| 14 | 14 | 14 |
| 16 | 73 | 79 |
| 17 | 32 | 31 |
| 21 | 25 | 25 |
| 22 | 97 | 92 |
| 23 | 29 | 29 |
| 24 | 50 | 50 |
| 25 | 51 | 56 |
| 26 | 59 | 61 |
| 27 | 91 | 86 |
| 28 | 10 | 10 |
| 29 | 26 | 30 |
| 31 | 98 | 93 |
| 36 | 74 | 78 |

TABLE 5-continued

| Compound | P. falciparum (K1) EC50 ng/mL | P. falciparum (NF54) EC50 ng/mL |
|---|---|---|
| 37 | 97 | 99 |
| 42 | 61 | 71 |
| 43 | 9.8 | 9.4 |
| 44 | 10 | 11 |
| 47 | 85 | 89 |
| 49 | 79 | 85 |
| 51 | 43 | 44 |
| 52 | 31 | 33 |
| 55 | 41 | 40 |
| 59 | 98 | 107 |
| 65 | 33 | 34 |
| 69 | 60 | 61 |
| 71 | 6.8 | 7.9 |
| 72 | 40 | 40 |
| 75 | 110 | 88 |
| 78 | 110 | 94 |
| 79 | 46 | 47 |
| 80 | 28 | 25 |
| 82 | 23 | 21 |
| 85 | 8.6 | 8.1 |
| 86 | 9.0 | 8.6 |

TABLE 6

| Compound | P. falciparum (3D7) % inhibition at 1.8 μM | P. falciparum (Dd2) % inhibition at 1.8 μM |
|---|---|---|
| 2 | 99 | 96 |
| 3 | 99 | 94 |
| 4 | 99 | 96 |
| 5 | 98 | 98 |
| 6 | 98 | 98 |
| 7 | 93 | 96 |
| 8 | 83 | |
| 9 | 76 | 53 |

These data show that aminopyridine derivatives according to the invention are able to inhibit parasite proliferation in infected human erythrocytes.

EXAMPLE 4

Anti-Malarial in Vivo Efficacy of Aminopyridines According to the Invention

The ability of aminopyridine derivatives according to the invention to show antimalarial efficacy in vivo can be tested by using the protocols described in the supplemental material to Fiddock et al., 2004, Nature Reviews Drug Discovery, (3), p 509.

The invention claimed is:
1. An aminopyridine selected from the following group:
(N,N-dimethyl){4-[2-amino-3-(2-methoxypyridin-5-yl) pyridin-5-yl]benzene}sulphonamide;
4-[2-amino-3-(2-methoxypyridin-5-yl)pyridin-5-yl]-N,N-dimethyl benzamide;
5-(2-methoxy pyridin-5-yl)-3-[4-(methylsulfonyl)phenyl] pyridin-2-amine;
5-[4-(methyl sulfonyl)phenyl]-3-(pyrimidin-5-yl)pyridin-2-amine;
(Morpholino){4-[2-amino-3-(2-methoxypyridin-5-yl)pyridin-5-yl]benzene}sulphonamide;
(N-methyl piperazin){4-[2-amino-3-(2-methoxypyridin-5-yl)pyridin-5-yl]benzene}sulphonamide;
3,5-di-[4-(methylsulfonyl)phenyl]pyridin-2-amine;
3-(2-methoxy pyridin-5-yl)-5-[3-(methyl sulfonyl)phenyl]pyridin-2-amine;
(N-methyl){4-[2-amino-3-(2-methoxypyridin-5-yl)pyridin-5 -yl]benzene}sulphonamide;
4-[2-amino-3-(2-methoxypyridin-5-yl)pyridin-5-yl]-N-methylbenzamide;
{4-[2-amino-3-(2-methoxy pyridin-5-yl)pyridin-5-yl]phenyl}(morpholino)methanone;
4-[2-amino-3-(2-methoxypyridin-5-yl)pyridin-5-yl]benzamide;
4-[6-amino-5-(2-methoxypyridin-5-yl)pyridin-3-yl]benzoic acid;
N-{4-[2-amino-3-(2-methoxy pyridin-5-yl) pyridin-5-yl]benzene}methyl sulphonamide;
4-[6-amino-5-(6-methoxypyridin-3-yl)pyridin-3-yl]-N-(3-hydroxypropyl)benzamide;
5-(benzo[c][1,2,5]oxadiazol-6-yl)-3-(2-methoxypyridin-5-yl)pyridin-2-amine;
N-cyclopropyl-{4-[2-amino-3-(2-methoxy pyridin-5-yl)pyridin-5-yl]benzene}sulphonamide;
5-(H-imidazo[1,2-a]pyridin-6-yl)-3-(2-methoxy pyridin-5-yl)pyridin-2-amine;
3-(2-methoxy pyridin-5-yl)-5-(1-methyl-1H-indazol-6-yl)pyridin-2-amine;
4-[2-amino-3-(2-methoxypyridin-5-yl)pyridin-5-yl]-N-(2-morpholino ethyl)benzamide;
3-[2-amino-3-(2-methoxypyridin-5-yl)pyridin-5-yl]benzamide;
3-(2-methoxypyridin-5-yl)-5-[4-(5-methyl-1,3,4-oxadiazol-2-yl)phenyl]pyridin-2-amine;
3-(2-methoxypyridin-5-yl)-5 -(6-morpholinopyridin-3-yl)pyridin-2-amine;
5-[4-(1H-pyrazol-1-yl)phenyl]-3-(2-methoxy pyridin-5-yl)pyridin-2-amine;
3-(2-methoxy pyridin-5-yl)-5-(quinolin-6-yl)pyridin-2-amine;
4-[2-amino-3-(2-methoxypyridin-5-yl)pyridin-5-yl]-N-[2-(pyrrolidin-1-yl)ethyl]benzamide;
5-[2-(trifluoro methyl)-4-(methylsulfonyl)phenyl]-3-(2-methoxypyridin-5-yl)pyridin-2-amine;
{4-[2-amino-3-(4-carbamoyl phenyl)pyridin-5-yl]phenyl}(morpholino)methanone;
4-[2-amino-3-(2-methylpyridin-5-yl)pyridin-5-yl]benzamide;
4-[2-amino-5-[4-(4-morpholinylcarbonyl)phenyl]-pyridin-3yl]-N-(2-hydroxyethyl)-benzamide;
4-[2-amino-3-(2-methoxypyridin-5-yl)pyridin-5-yl]benzene sulphonamide;
4-[2-amino-3-(4-benzamido)pyridin-5-yl]benzamide;
{4-[2-amino-3-(2-methoxypyridin-5-yl)pyridin-5-yl]phenyl}(4-methylpiperazin-1-yl)methanone;
4-[2-amino-3-(2-methoxypyridin-5-yl)pyridin-5-yl]-N-[4-(aminomethyl)thiazol-2-yl]benzamide;
{4-[2-amino-3-(4-(trifluoromethyl)phenyl)pyridin-5-yl]phenyl}(morpholino)methanone;
3-(2-methoxy pyridin-3-yl)-5-[4-(methyl sulfonyl phenyl]pyridin-2-amine;
5-[4-(methyl sulfonyl)phenyl]-3-(pyridin-3-yl)pyridin-2-amine;
4-{2-amino-5-[4-(methyl sulfonyl)phenyl]pyridin-3-yl}benzonitrile;
3-{2-amino-5-[4-(methylsulfonyl)phenyl]pyridin-3-yl}benzonitrile;
4-{2-amino-5-[4-(methylsulfonyl)phenyl]pyridin-3-yl}benzamide;
4-{2-amino-5-[4-(methylsulfonyl)phenyl]pyridin-3- yl}-N-methylbenzamide;

3-(H-imidazo[1,2-a]pyridin-6-yl)-5-[4-(methyl sulfonyl)phenyl]pyridin-2-amine;
3-(2-methoxy pyrimidin-5-yl)-5-[4-(methylsulfonyl)phenyl]pyridin-2-amine;
5-[4-(methyl sulfonyl)phenyl]-3-(quinoxalin-7-yl)pyridin-2-amine;
3-(furan-3-yl)-5-[4-(methylsulfonyl)phenyl]pyridin-2-amine;
3-[4-(5-methyl-1,3,4-oxadiazol-2-. yl)phenyl]-5-[4-(methylsulfonyl)phenyl]pyridin-2-amine;
3-(3-chloro-2-methoxypyridin-5-yl)-5-[4-(methylsulfonyl)phenyl]pyridin-2-amine;
5-[4-(methylsulfonyl)phenyl]-3-[3-(trifluoromethoxy)phenyl]pyridin-2-amine;
5-[4-(methylsulfonyephenyl]-3-[4-(trifluoromethoxy)phenyl]pyridin-2-amine;
5-[4-(methylsulfonyl)phenyl]-3-[2-(pyrrolidin-1-yl)pyridin-5-yl]pyridin-2-amine;
3-[2-chloro-4-(trifluoromethyl)phenyl]-5-[4-(methylsulfonyl)phenyl]pyridin-2-amine;
3-(3-methoxy pyridin-4-yl)-5-[4-(methylsulfonyl)phenyl]pyridin-2-amine;
5-[4-(methylsulfonyl)phenyl]-3-(2-morpholino pyridin-5-yl)pyridin-2-amine;
3-[2-(trifluoromethyl)pyridin-4-yl]-5-[4-(methylsulfonyl)phenyl]pyridin-2-amine;
3-(2-methylpyridin-5-yl)-5-[4-(methyl sulfonyl)phenyl]pyridin-2-amine;
3-[2-(trifluoro methyl)pyridin-5-yl]-5-[4-(methyl sulfonyl)phenyl]pyridin-2-amine;
3-{4-[2-(pyrrolidin-1-ypethoxy]phenyl}-5-[4-(methylsulfonyl)phenyl]pyridin-2-amine;
5-[4-(methyl sulfonyl)phenyl]-3-(4-. morpholinopheny)pyridin-2-amine;
3-[4-(1H-pyrazol-1-yl)phenyl]-5-[4-(methylsulfonyl)phenyl]pyridin-2-amine;
5-{2-amino-5-[4-(methylsulfonyl)phenyl]pyridin-3-yl}pyrimidin-2-amine;
3-{2-amino-5-[4-(methylsulfonyl)phenyl]pyridin-3-yl}benzamide;
3-(6-methoxy-2-methylpyridin-3-yl)-5-[4-(methylsulfonyl)phenyl]pyridin-2-amine;
3-(isoquinolin-5-yl)-5-[4-(methyl sulfonyl)phenyl]pyridin-2-amine;
5-[4-(methyl sulfonyl)phenyl]-3-(quinolin-6-yl)pyridin-2-amine;
5-[4-(methylsulfonyl)phenyl]-3-p-tolylpyridin-2-amine;
{5-[2-amino-5-(4-(methylsulfonyl)phenyl)pyridin-3-yl]pyridin-2-. yl}methanol;
3-(2-methylbenzo[d]thiazol-5-yl)-5-[4-(methylsulfonyl)phenyl]pyridin-2-amine;
N-{4-[2-amino-5-(4-(methylsulfonyl)phenyl)pyridin-3-yl]phenyl}-2-(dimethylamino)acetamide;
3-(2-fluoropyridin-5-yl)-5-[4-(methylsulfonyl)phenyl]pyridin-2-amine;
5-[4-(methylsulfonyl)phenyl]-3-[2-(methylsulfonyl)pyridin-5-yl]pyridin-2-amine;
N-{5-[2-amino-5-(4-(methylsulfonyl)phenyl)pyridin-3-yl]pyridin-2-yl}acetamide;
3-(benzo[c][1,2,5]oxadiazol-5-yl)-5-[4-(methylsulfonyl)phenyl]pyridin-2-amine;
3-{2-amino-5-[4-(methylsulfonyl)phenyl]pyridin-3-yl]-N-(2-hydroxyethyl)benzamide;
3-[4-(trifluoromethyl)phenyl]-5-[4-(methylsulfonyl)phenyl]pyridin-2-amine;
3-(3-methylpyridin-5-yl)-5-[4-(methylsulfonyl)phenyl]pyridin-2-amine; or
5-[3-fluoro-4-(methylsulfonyl)phenyl]-3-(2-methoxypyridin-5-yl)pyridin-2-amine.

2. A pharmaceutical formulation containing at least one aminopyridine according to claim 1 and a pharmaceutically acceptable carrier, diluent or excipient.

3. A pharmaceutical formulation containing at least one aminopyridine according to claim 1 and a pharmaceutically acceptable carrier, diluent or excipient and a co-agent useful in the treatment of malaria.

4. A method for treating malaria, wherein the method comprises administering an effective amount of an aminopyridine according to claim 1 to a patient in need thereof.

5. The method according to claim 4, wherein the aminopyridine is administered in combination with a co-agent useful in the treatment of malaria.

6. An aminopyridine selected from the following group:
3-(6-Methoxypyridin-3-yl)-5-(4-methylsulfonylphenyl)pyridin-2-amine;
5-(4-methylsulfonylphenyl)-3-[3-(trifluoromethyl)phenyl]pyridin-2-amine;
3-[2-amino-5-(4-methylsulfonylphenyl)pyridin-3-yl]phenol;
4-[2-amino-5-(4-methylsulfonylphenyl)pyridin-3-yl]-2-methoxyphenol;
4-[2-amino-5-(6-methoxypyridin-3-yl)pyridin-3-yl]-2-methoxyphenol;
4-[6-amino-5-[4-(4-methylpiperazin-1-yl)phenyl]pyridin-3-yl]-2,6-dimethylphenol;
[4-[6-amino-5-(6-methoxypyridin-3-yl)pyridin-3-yl]phenyl]methanol; or
4-[6-amino-5-[4-(4-methylpiperazin-1-yl)phenyl]pyridin-3-yl]phenol.

7. A pharmaceutical formulation containing at least one aminopyridine according to claim 6 and a pharmaceutically acceptable carrier, diluent or excipient.

8. A pharmaceutical formulation containing at least one aminopyridine according to claim 6 and a pharmaceutically acceptable carrier, diluent or excipient and a co-agent useful in the treatment of malaria.

9. A method for treating malaria, wherein the method comprises administering an effective amount of an aminopyridine according to claim 6 to a patient in need thereof.

10. The method according to claim 9, wherein the aminopyridine is administered in combination with a co-agent useful in the treatment of malaria.

* * * * *

UNITED STATES PATENT AND TRADEMARK OFFICE
CERTIFICATE OF CORRECTION

PATENT NO. : 9,024,033 B2
APPLICATION NO. : 13/522775
DATED : May 5, 2015
INVENTOR(S) : Michael John Witty and David Hardick It is certified that error appears in the above-identified patent and that said Letters Patent is hereby corrected as shown below:

Specification

Column 2,
Line 63, "2-butyryl," should read --2-butynyl,--.

Column 4,
Line 53, ""hetero aryl,"" should read --"heteroaryl,"--.
Line 64, ""hetero aryl,"" should read --"heteroaryl,"--.

Column 5,
Line 18, ""hetero aryl,"" should read --"heteroaryl,"--.
Line 49, ""heteroarylaryl $C_1$-$C_6$" should read --"heteroaryl $C_1$-$C_6$--.

Column 6,
Line 5, ""hetero aryl,"" should read --"heteroaryl,"--.
Line 14, "a –$SF_S$" should read --a –$SF_5$--.
Line 18, ""hetero aryl,"" should read --"heteroaryl,"--.
Line 22, "$C_1$—$O_5$-alkyl" should read --$C_1$-$C_5$-alkyl--.

Column 9,
Lines 37-38, "3-(2-methoxy pyridin-5-yl)-5-(1-methyl-1H-indazol-6-yl)pyridin-2-amine"
    should read
        --3-(2-methoxy pyridin-3-yl)-5-(1-methyl-1H-indazol-6-yl)pyridin-2-amine--.

Column 17,
Lines 27-28, "3-(2-methoxy pyridin-5-yl)-5-(1-methyl-1H-indazol-6-yl)pyridin-2-amine"
    should read
        --3-(2-methoxy pyridin-3-yl)-5-(1-methyl-1H-indazol-6-yl)pyridin-2-amine--.

Signed and Sealed this
Twenty-third Day of February, 2016

Michelle K. Lee
*Director of the United States Patent and Trademark Office*

Specification

Column 61, No. 39, Chemical name,
Lines 22-27, "3-[2-chloro-4-(trifluoromethyl)phenyl]-5-[4-(methyl sulfonyl) phenyl] pyridine-2-amine" should read
--3-[2-chloro-4-(trifluoromethyl)phenyl]-5-[4-(methyl sulfonyl) phenyl] pyridin-2-amine--.

Column 78,
Line 38, "OPERATM" should read --OPERA™--.

Claims

Column 80,
Lines 60-61, Claim 1, "4-{2-amino-5-[4-(methyl sulfonyl)phenyl]pyridin-3-yl}benzonitrile;" should read
--4-{2-amino-5-[4-(methylsulfonyl)phenyl]pyridin-3-yl}benzonitrile;--.

Column 81,
Lines 15-16, Claim 1, "5-[4-(methylsulfonyephenyl]-3-[4-(trifluoromethoxy)phenyl]pyridin-2-amine;" should read
--5-[4-(methylsulfonyl)phenyl]-3-[4-(trifluoromethoxy)phenyl]pyridin-2-amine;--.
Lines 31-32, Claim 1, "3-{4-[2-(pyrrolidin-1-ypethoxy]phenyl}-5-[4-(methylsulfonyl)phenyl] pyridin-2-amine;" should read
--3-{4-[2-(pyrrolidin-1-yl)ethoxy]phenyl}-5-[4-(methylsulfonyl)phenyl] pyridin-2-amine;--.